United States Patent
Kietzmann et al.

(10) Patent No.: US 12,374,453 B2
(45) Date of Patent: Jul. 29, 2025

(54) SYSTEM AND METHOD FOR SCANNING AND CONTROLLING STORAGE OF AN INJECTION DEVICE

(71) Applicant: Sanofi, Paris (FR)

(72) Inventors: Hardy Kietzmann, Frankfurt am Main (DE); Pablo Prados, Paris (FR)

(73) Assignee: Sanofi, Paris (FR)

( * ) Notice: Subject to any disclaimer, the term of this patent is extended or adjusted under 35 U.S.C. 154(b) by 132 days.

(21) Appl. No.: 18/039,058

(22) PCT Filed: Dec. 1, 2021

(86) PCT No.: PCT/EP2021/083679
§ 371 (c)(1),
(2) Date: May 26, 2023

(87) PCT Pub. No.: WO2022/117603
PCT Pub. Date: Jun. 9, 2022

(65) Prior Publication Data
US 2024/0055115 A1 Feb. 15, 2024

(30) Foreign Application Priority Data
Dec. 2, 2020 (EP) .................................... 20315482

(51) Int. Cl.
*G08B 21/02* (2006.01)
*G08B 5/36* (2006.01)
(Continued)

(52) U.S. Cl.
CPC ............... *G16H 40/63* (2018.01); *G08B 5/36* (2013.01); *G16H 20/17* (2018.01)

(58) Field of Classification Search
USPC ............ 340/539.11, 539.12, 539.13, 539.22, 340/539.32, 571, 636.19, 3.3, 3.6, 5.91
See application file for complete search history.

(56) References Cited

U.S. PATENT DOCUMENTS 8,678,047 B2 * 3/2014 Tribble .................. A61J 3/002
  141/27
9,382,021 B2 * 7/2016 Tribble ................ A61J 1/2096
(Continued)

FOREIGN PATENT DOCUMENTS

JP   2020-508752   3/2020
JP   2020-510469   4/2020
(Continued)

OTHER PUBLICATIONS

International Preliminary Report on Patentability in International Appln. No. PCT/EP2021/083679, mailed on Jun. 15, 2023, 11 pages.
(Continued)

*Primary Examiner* — Daniel Previl
(74) *Attorney, Agent, or Firm* — Fish & Richardson P.C.

(57) ABSTRACT

A system including a user device and a storage device communicating wirelessly with each other. The user device includes a processor, a memory, and a wireless transceiver. The storage device includes multiple openings, each opening being configured to store an unused injection device for a period of time and wherein each opening has an associated sensor, and a storage device wireless transceiver. The user device can be configured to scan a first injection device to determine at least one of a drug dosage contained within the first injection device and a device expiration date of the first injection device, and to create first device data relating to the drug dosage and the device expiration date and to associate the first device data with a first opening of the plurality of openings of the storage device.

20 Claims, 11 Drawing Sheets

(51) Int. Cl.
*G16H 20/17* (2018.01)
*G16H 40/63* (2018.01)

(56) References Cited

U.S. PATENT DOCUMENTS

| | | | |
|---|---|---|---|
| 10,327,988 B2 * | 6/2019 | Tribble | B65B 3/003 |
| 2005/0055242 A1 * | 3/2005 | Bello | G16H 20/17 |
| | | | 705/2 |
| 2017/0079734 A1 | 3/2017 | Denny et al. | |
| 2017/0106142 A1 * | 4/2017 | Hochman | A61M 5/172 |
| 2017/0312457 A1 * | 11/2017 | DeSalvo | G09B 19/24 |
| 2018/0333543 A1 * | 11/2018 | Diaz | A61M 5/172 |

FOREIGN PATENT DOCUMENTS

| | | |
|---|---|---|
| WO | WO 2018/153945 | 8/2018 |
| WO | WO 2018/154033 | 8/2018 |
| WO | WO 2022/117603 | 6/2022 |

OTHER PUBLICATIONS

International Search Report and Written Opinion in International Appln. No. PCT/EP2021/083679, mailed on Feb. 23, 2022, 13 pages.

\* cited by examiner

SYSTEM AND METHOD FOR SCANNING AND CONTROLLING STORAGE OF AN INJECTION DEVICE

CROSS REFERENCE TO RELATED APPLICATIONS

The present application is the national stage entry of International Patent Application No. PCT/EP2021/083679, filed on Dec. 1, 2021, and claims priority to Application No. EP 20315482.8, filed on Dec. 2, 2020, the disclosures of which are incorporated herein by reference.

TECHNICAL FIELD

The present disclosure relates to systems and tools including a user device and a storage device configured to communicate wirelessly with each other so as to scan injection devices and determine the placement of the injection devices within the storage device.

BACKGROUND

Patients suffering chronic disease often require regular treatment with medicaments, e.g., on the basis of a pre-defined schedule. Particular medicaments require refrigerated storage, and are often stored for extended periods of time in a household refrigerator or fridge. In a home treatment environment, the patient stores the medicament in their fridge and self-administers a predefined dose as required. Hence, the medicament is typically provided in a secondary packaging for convenient placement and storage in the household fridge.

A medicament may have a predefined dosing schedule which requires the administration of a dose at relatively long intervals, for instance every two or four weeks. The medicament may be provided in a secondary packaging containing several doses which may be stored in the fridge for 1 to 6 months for instance. It can be difficult for patients to keep track of each scheduled dosing time, which can lead to poor adherence with a prescribed dosage regimen. Furthermore, for some long acting medicaments, the user may be generally symptom free at the prescribed time of their next injection, which can lead to a further risk of non-adherence to a prescribed dosage regimen. In addition, during the course of such a treatment, the scheduled dosing may need adjustment after consultation with a Health Care Professional (HCP).

SUMMARY

Aspects of this disclosure relate to different types of injection devices that may contain different dosages of medicament. And treatments may require the use of more than one type of injection device. For example, a higher "initial dose" may be needed, followed by frequent lower "maintenance doses". Certain medicaments may require injection at a specific temperature or within a specific temperature range. It may also be important that certain medicaments are taken at certain times of the day, before or after meals, or with or without other therapies. As such, it can be important to accurately track the use of a specific injection device to confirm that a patient has used it appropriately. These and other advantages will be described in the currently disclosed systems and tools.

Some injection device storage devices are capable of storing many individual injection devices. In some instances the user may even store different medicaments in the same storage device or different dosages of the same medicament. There is therefore the possibility for the user to select an incorrect injection device and for mis-administration of medicament to occur. In situations where an injection device is stored for a prolonged period, it is also possible for the medicament contained therein to exceed its expiry date if the order of use of the injection devices is not controlled. These problems are alleviated by the currently disclosed system and method.

A first aspect disclosed herein requires a system comprising a user device and a storage device configured to communicate wirelessly with each other, the user device comprising: a processor; a memory; and a wireless transceiver, the storage device comprising: a plurality of openings, wherein each opening is configured to store an unused injection device for a period of time and wherein each opening has an associated sensor; and a storage device wireless transceiver wherein the user device is configured to: scan a first injection device to determine at least one of a drug dosage contained within the first injection device and a device expiration date of the first injection device; and create first device data relating to at least one of the drug dosage and the device expiration date and associate the first device data with a first opening of the plurality of openings of the storage device, wherein the storage device is configured to: detect whether the first injection device has been placed in, or removed from, the first opening.

The storage device may be configured to send a signal to the user device indicating which one of the plurality of openings an injection device was placed in or removed from.

Having the user device monitor and determine the specific opening into which injection devices are placed allows the user device to act as a safety check that a correct injection device is subsequently used so as to reduce the likelihood of a mis-dosing, or to encourage the use of an injection device having an earliest expiry date, so as to reduce the chance of medicament being wasted. Where users need to use two or more injection devices in a single dosing episode, the user device can act as a guide for this process, potentially improving user confidence and adherence to the prescribed dosage regimen.

The created first device data may be transmitted by the user device to an external database, Healthcare Professional or patient support programme.

The user device may be configured: subsequent to receiving the signal from the storage device, to confirm whether the first injection device was placed in or removed from the first opening or a different opening; if the first injection device was placed in or removed from the first opening, to output a confirmation message; and if the first injection device was placed in or removed from a different opening, to output an alert.

The user device may also send an alert message to an external device or server, so that the alert is received by a Healthcare Professional or by the user's patient support programme. Action, such as contacting the user directly, could then be taken if it is suspected that a mis-dosing event may have occurred.

Each associated sensor may be configured to determine an ID of an injection device stored in the associated opening and the storage device may be configured to send a signal to the user device indicating which one of the plurality of openings an injection device was placed in or removed from and the ID of the injection device.

The user device may be configured to transmit to the storage device an indication of which of the plurality of openings is the first opening.

Each of the plurality of openings may have at least one associated LED and after receiving the indication of which of the plurality of openings is the first opening from the user device, the storage device may be configured to illuminate one or more of the at least one LED associated with the first opening.

The user device may be configured to: display a representation of the storage device; indicate which of the plurality of openings is the first opening on the representation; and indicate that the first injection device should be placed into the first opening on the representation.

Upon determining that an injection is due, the user device may be configured to indicate on the representation of the storage device which of the plurality of openings to remove an injection device from.

Upon determining that an injection is due, the user device may be configured to transmit to the storage device an indication of which of the plurality of openings to remove an injection device from. Each of the plurality of openings may have at least one associated LED and after receiving from the user device the indication of which of the plurality of openings to remove an injection device from, the storage device may be configured to illuminate one or more of the at least one LED associated with the indicated opening.

Upon determining that the storage device contains several injection devices having the same drug dosage, the user device may be configured to select the injection device having the earliest expiration date and to indicate the opening containing the injection device having the earliest expiration date on the representation of the storage device and/or by transmitting the indication to the storage device.

Upon determining that two different injection devices need to be used, the user device may be configured to indicate two openings of the storage device and to differentiate between the two openings on the representation of the storage device and/or by signalling to the storage device.

The user device may be configured to indicate an order in which the two different injection devices need to be used on the representation of the storage device and/or by signalling to the storage device.

The user device may be configured to: scan a second injection device to determine at least one of a drug dosage contained within the second injection device and a device expiration date of the second injection device; create second device data relating to at least one of the drug dosage and the device expiration date and associate the second device data with a second opening of the plurality of openings of the storage device, and the storage device may be configured to: detect whether the second injection device has been placed in, or removed from, the second opening.

A second aspect disclosed herein requires a method of operating a user device and a storage device configured to communicate wirelessly with each other, the user device comprising: a processor;
    a memory; and a wireless transceiver, the storage device comprising: a plurality of openings, wherein each opening is configured to store an unused injection device for a period of time and wherein each opening has an associated sensor; and a storage device wireless transceiver wherein the method comprises the user device: scanning a first injection device to determine at least one of a drug dosage contained within the first injection device and a device expiration date of the first injection device; and creating first device data relating to at least one of the drug dosage and the device expiration date and associate the first device data with a first opening of the plurality of openings of the storage device, wherein method comprises the storage device: detecting whether the first injection device has been placed in, or removed from, the first opening.

DETAILED DESCRIPTION

Overall Digital System Description

Figure 1:
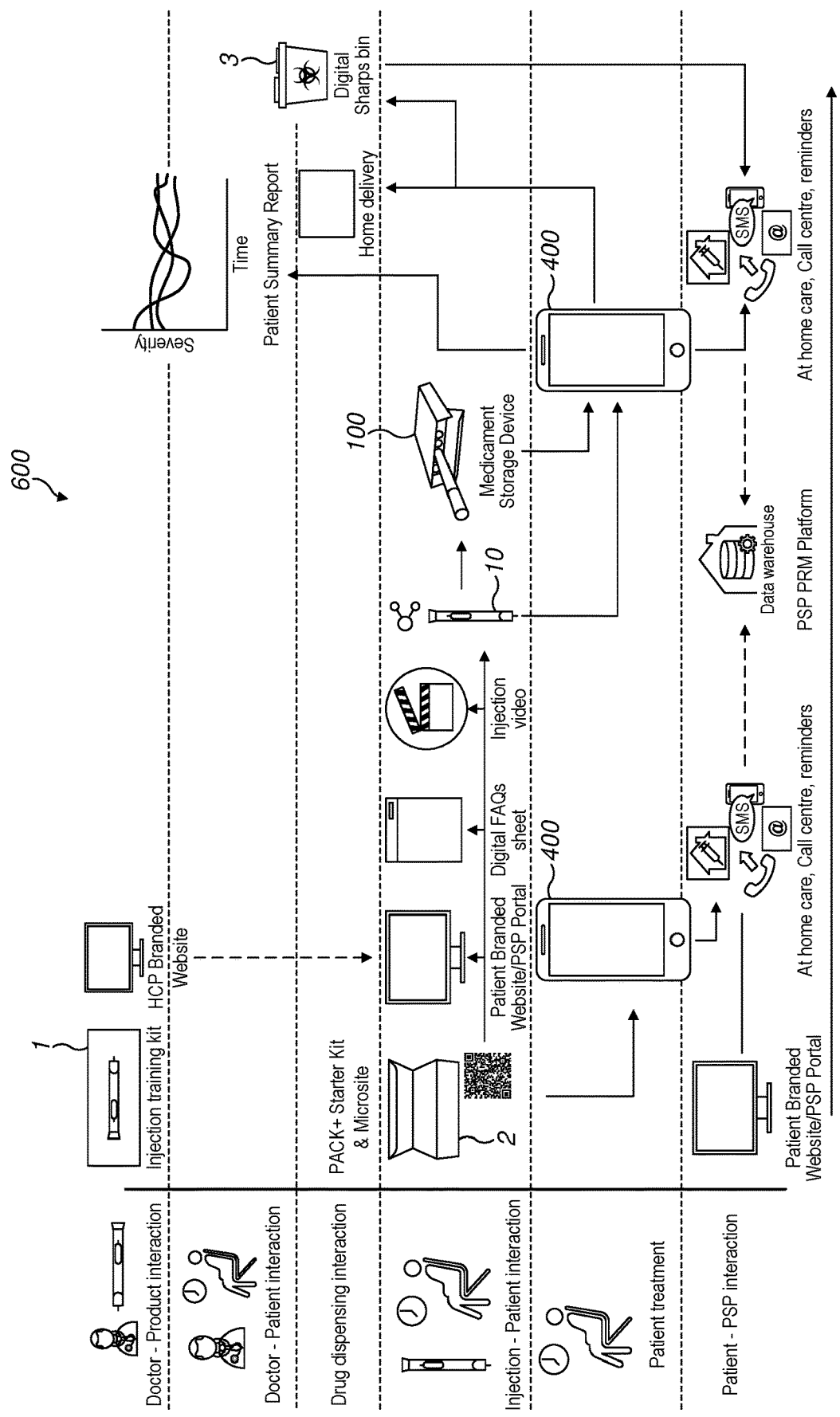
FIG. 1 is a schematic illustration of a digital system including a user device, an injection device, a disposal device, and a storage device according to some embodiments.

With reference to FIG. 1, a device and digital system 600 is schematically illustrated. System 600 may comprise various devices and digital sub-systems. The various devices can include one or more injection devices 10, a storage device 100 configured to store one or more injection devices 10, and a sharps bin 3 configured to receive one or more used injection devices 10. System 600 may also include a user device 400 configured to interact with one or more of injection devices 10, storage device 100, and sharps bin 3. For example, user device 400 may communicate wirelessly with the one or more injection devices 10, storage device 100, and sharps bin 3. Communication between user device 400 and injection device 10 can include a patient scanning a label (not shown) of injection device 10 with user device 400.

User device 400 may further communicate with one or more digital sub-systems to receive or transmit information related to one or more injection devices 10, storage device 100, and sharps bin 3. This can include, for example, tracking one or more steps from the patient receiving injection device 10, successfully administering a medicament contained within injection device 10, through to disposal of injection device 10.

Once a patient has received injection device 10, they may place the device in storage device 100. As explained below, storage device 100 may be configured to receive and store one or more unused injection devices 10. Many medicaments for treatment of chronic diseases require storage at less than room temperature. Consequently, storage device 100 is often mounted in a refrigerator of a patient.

For effective treatment of a chronic condition, a doctor or HCP may need to monitor the progressive use of injection device 10 as it is used by a patient. This can include determining when injection device 10 was removed from a fridge, allowed to come to room temperature (or any other temperature that could be considered operational temperature of the injection device 10), operated by a patient, confirmed injection was successful, and safely disposed of.

As the patient needs to self-inject, they may take a specific injection device 10 from storage device 100. Storage device 100 and/or injection device 10 may communicate with user device 400 to provide one or more time-stamps, or other indications of when a patient removed an injection device 10 from storage device 100.

For a single patient, multiple data received from multiple sources can provide more accurate and consistent information for a doctor or HCP. Similarly, multiple data inputs from user device 400, storage device 100, and/or sharps bin 3 can confirm that the specific injection device 10 was properly used and disposed of.

These and other advantages of system 600 are described below. In some embodiments, injection devices 10 may include a medicament for chronic treatment of atopic dermatitis. The system diagram of FIG. 1 illustrates the flow of information and interactions between different elements of system 600.

Training Kit

The contexts of the interactions are illustrated on the left side of FIG. 1. For example, a doctor or other Health Care Profession (HCP) may provide an injection training kit 1 to a patient. The training kit may comprise a training injection device and instructions on how to operate the injection device. The doctor/HCP may also access a HCP specific website for further information and training and to enter patient specific information.

Any patient specific information entered by the HCP on the HCP specific website may be communicated to a patient website which the patient may access via their personal profile. The patient website may contain resources to aid the user in safely using the injection device 10 and storage device 100, including training videos.

The patient may receive ongoing support in the form of a patient support programme (PSP). Lack of adherence to a prescribed injection regimen is a major issue for providing effective treatment to patients, especially where the interval between injection is long (such as, for example, 1, 2, 4, 6, 8, or more weeks). In one example of a patient support programme, the patient receives an introduction call before or at the same time as receiving their first injection device 10 or set of injection devices. The purpose of the introductory call is to explain the programme and discuss expectations, allow the patient and/or caregiver to select the components of the programme, complete questionnaires and the Patient Activation Measure (an estimation of the risk of non-adherence), address any immediate concerns or worries with the patient and/or caregiver, confirm the date and time of the first follow up calls and confirm with patient and/or caregiver the level of support they will receive.

The patient may then receive a nurse visit and injection training. This may comprise a single visit, or up to three visits by the nurse. In some examples of a patient support programme, the nurse visit(s) may occur before the introduction call. The Patient Activation Measure (PAM) may have one of four different levels indication different risk levels of non-adherence with a prescribed dosing regimen. All levels may comprise provide a quarterly review call with the patient. For those patients with the lowest risk of non-adherence (PAM level 4), a call may be made after every injection for a predetermined time, for example the first four weeks and discontinued after that. For those patients with a low risk of non-adherence (PAM level 3), after the calls made after every injection for a predetermined time, the patient may receive a support call every eight weeks. For those with a high risk of non-adherence (PAM level 2), the support call after every injection may be continued for a longer period of time, for example for eight weeks and may be provided every month thereafter. PAM level 2 may also comprise two motivational interviews each year. For those with a very high risk of non-adherence (PAM level 1), a support call may be provided after every injection, for example five days after each injection. A number of motivational calls may be provided each year, for example three or four each year.

One of the advantages of the patient support programme, training kit and other features of the system descried herein is that they increase patient adherence with their prescribed medicament regimen. In one trial of 3633 patients, 90% were enrolled onto a homecare support programme and 70% were enrolled onto the homecare support programme including home delivery of injection devices. The overall adherence rate of this patient group was 91%, showing a marked increase in adherence when compared with no support programme.

Starter Kit

The patient can be provided with an injection device 10 and starter kit 2. As well as printed material, the starter kit 2 may comprise a microsite containing key information relating to operation of the injection device 10 and storage device 100 and a link to download the application accompanying the storage device 100. The starter kit may comprise only the storage device 100, while the injection devices 10 are provided separately. Alternatively, the starter kit 2 may contain a supply of injection devices 10 in addition to the storage device 100.

The patient may use their user device 400 (which may be a smartphone, tablet or similar device) to access the microsite, for example by scanning a QR code. The microsite may contain videos to teach a user how to self inject with the injection devices 10, a virtual reality programme, which may allow the user to be shown a virtual version of the injection device 10 in operation, digital FAQs and answers, a link to the patient website and a link to download the application. The microsite may require a patient to enter certain personal information such as an email address. An email may then be sent to the patient's email address with a link to download the application onto one or more user devices 400.

A piece of card which can be folded into a phone holder may be provided with the starter kit. The user may select the virtual reality program from the microsite and place their phone in the phone holder provided. The virtual reality programme may contain virtual consultations with a nurse and/or consultant, an animation of the skin to demonstrate the cause of certain skin conditions and the role of biologics, a 3D injection technique animation including 3D model of the syringe, a series of infographics and virtual objects to aid retention, FAQs and further resources.

As illustrated, the patient may obtain support via the patient website, via a call centre, text reminders and/or through at home care.

User Device

In some embodiments, the user device 400 is a smartphone or tablet. However, the user device 400 may be embodied as a laptop, a smart display such as a Nest Hub, a smart speaker (e.g., Amazon Echo or similar voice-activated device), a smart TV, a smart watch or other wearable device such as a headset or glasses, or a connected fridge. The user device 400 may download the application from a digital store, or it may be pre-programmed with the application. Different versions of the application may exist for use with the various devices mentioned above. The user may download the application onto multiple user devices and a single digital profile may ensure that information entered or updated on one device is synchronised with the other devices.

After downloading the application, the user may set or override certain information on the storage device 100, as described in greater detail below. Operational information may be communicated to the user device 400 by the storage device 100, such as the number of injection devices 10 stored in the storage device 100, days remaining until a next injection is due, temperature (e.g., local temperature, which, according to the context, may mean the temperature of the storage device 100, the injection device 10, the medicament, or any combination thereof), humidity and battery level. When the user needs to order more injection devices 10, this can be accomplished using the application and the new supply of injection devices 10 can be delivered to the patient's home. The application may then provide notifications when the injection devices 10 have been dispatched and when they are due to be delivered. Such notifications are particularly beneficial where the medicament contained in the injection devices 10 must be kept below a certain temperature, e.g., kept refrigerated.

The user device 400 may also be connected to one or more storage devices 100, and/or digital sharps bins 3. The user device 400 is configured to communicate wirelessly using a wireless communication protocol. For example, the first external device may communicate wirelessly using Wi-Fi, Bluetooth, ZigBee, IrDA or similar. The user device 400 may communicated with each of the other connected parts of the system 1000 in different ways. For example, the user device 400 may communicate directly (peer-to-peer) with the storage device 100 using Bluetooth. Alternatively, or in addition, the user device 400 may communicate with the storage device 100 via a wireless access point, using WiFi. The user device 400 may communicate with the injection device 10 using NFC. For example, the user device 400 may act as the reader and the injection device 10 as the target. Alternatively, the injection device 10 may be read optically, using Infrared or magnetically by the user device 400.

The user device 400 may communicate directly with the digital sharps bin 3, for example using Bluetooth. Alternatively, or in addition, the user device 400 may communicate with the digital sharps bin 3 via a wireless access point, using WiFi.

Injection Devices

Injection device 10, as described herein, may be configured to inject a medicament into a patient. For example, delivery could be sub-cutaneous, intra-muscular, or intravenous. Such a device could be operated by a patient or care-giver, such as a nurse or physician, and can include various types of pre-filed syringe, safety system, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml, or more).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

Injection devices 10 described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some injection devices 10 can include one or more functions of a safety system, pen-injector, or auto-injector. For example, injection device 10 could include a mechanical energy source configured to automatically inject a medicament (as typically found in an auto-injector) and a dose setting mechanism (as typically found in a pen-injector).

According to some embodiments, injection device 10 includes a housing which typically contains a reservoir containing the medicament to be injected (e.g., a syringe) and the components required to facilitate one or more steps of the delivery process. Injection device 10 can also include a cap assembly that can be detachably mounted to the housing. Typically a user must remove cap from housing before device 10 can be operated.

The housing of the injection device 10 has a distal region and a proximal region. The term "distal" refers to a location that is relatively closer to a needle or a site of injection, and the term "proximal" refers to a location that is relatively further away from the needle or injection site.

Device 10 can also include a needle sleeve coupled to the housing to permit movement of the sleeve relative to the housing. For example, the sleeve can move in a longitudinal direction parallel to a longitudinal axis. Specifically, movement of the sleeve in a proximal direction can permit a needle to extend from the distal region of the housing.

Injection device 10 may contain a label which can be read by another device and contain encoded information. The label may be provided externally or internally on the injection device 10. For example, the label of injection device 10 may be read by the user device 400 using NFC. The label may include a barcode, QR code or other optically encoded information which is read optically by the user device 400. Alternatively, or in addition, the injection device 10 may have information encoded magnetically. The injection device 10 may be scanned or otherwise read by the user device 400 before an injection takes place, after an injection takes place or before each injection device 10 is placed into the storage device 100. These and various other ways of tagging injection device 10 with information are contemplated. Various types of information may be included in the label. These can include the type of medicament or injection device, manufacturing source, expiration date, dose, country of origin, etc.

In some embodiments, injection device 10 may include a wireless communication module. This may allow injection device 10 to connect and communicate directly with the user device 400. The injection device may also communicate directly with the storage device 100 and/or the digital sharps bin 3.

Digital Sharps Bin

The digital system 600 may also comprise a digital sharps bin 3 which can determine when a spent injection device 10 is deposited inside. The digital sharps bin 3 may comprise one or more sensors located around or near an opening through which the used injection devices 10 are deposited. The sensor may be configured to read the information provided on the tag of each injection device as it is deposited in the bin. The digital sharps bin 3 may create a time stamp indicating the time of disposal of the injection device 10 and the contents of the injection device. The digital sharps bin 3 may immediately or periodically send this information to the user device 400. The digital sharps bin 3 may store an injection regimen for the user. This regimen may be updated using the application on the user device 400. If the digital sharps bin 3 determines that an injection device 10 has been deposited in the bin on a day or at a time when an injection is not scheduled according to the regimen, it may send an alert to the user device 400. The application on the user device 400 may also provide connectivity with the digital sharps bin 3 to act as the primary record or double check of the user's injection history. The digital sharps bin 3 may also be configured to send reminders via the application on the user device 400 when the next injection is due and to store locally data about the user's compliance with their injection schedule.

The digital sharps bin may also comprise a display, such as an LCD, and/or one or more LEDs. The LCD may be a touch sensitive display. The digital sharps bin 3 may also comprise a speaker and one or more user inputs in addition to a touch sensitive display. The display may activate whenever an injection device is deposited into the digital sharps bin 3. The display may show the patient's recent injection history and/or future injection regimen. The digital sharps bin 3 may receive information on the number of injection devices 10 remaining in the storage device 100, either directly form the storage device 100 or via the application on the user device 400. This information may also be displayed and a reminder to order more injection devices if appropriate. Any alerts related to an unexpected deposition of an injection device may also be displayed on the display and/or communicated audibly with the speaker.

Storage Device

The storage device 100 may be configured to detect when an injection device 10 is inserted or removed via labels provided on the injection devices 10. The storage device 100 may be configured to synchronise this information with the application on the user device 400.

Figure 7:
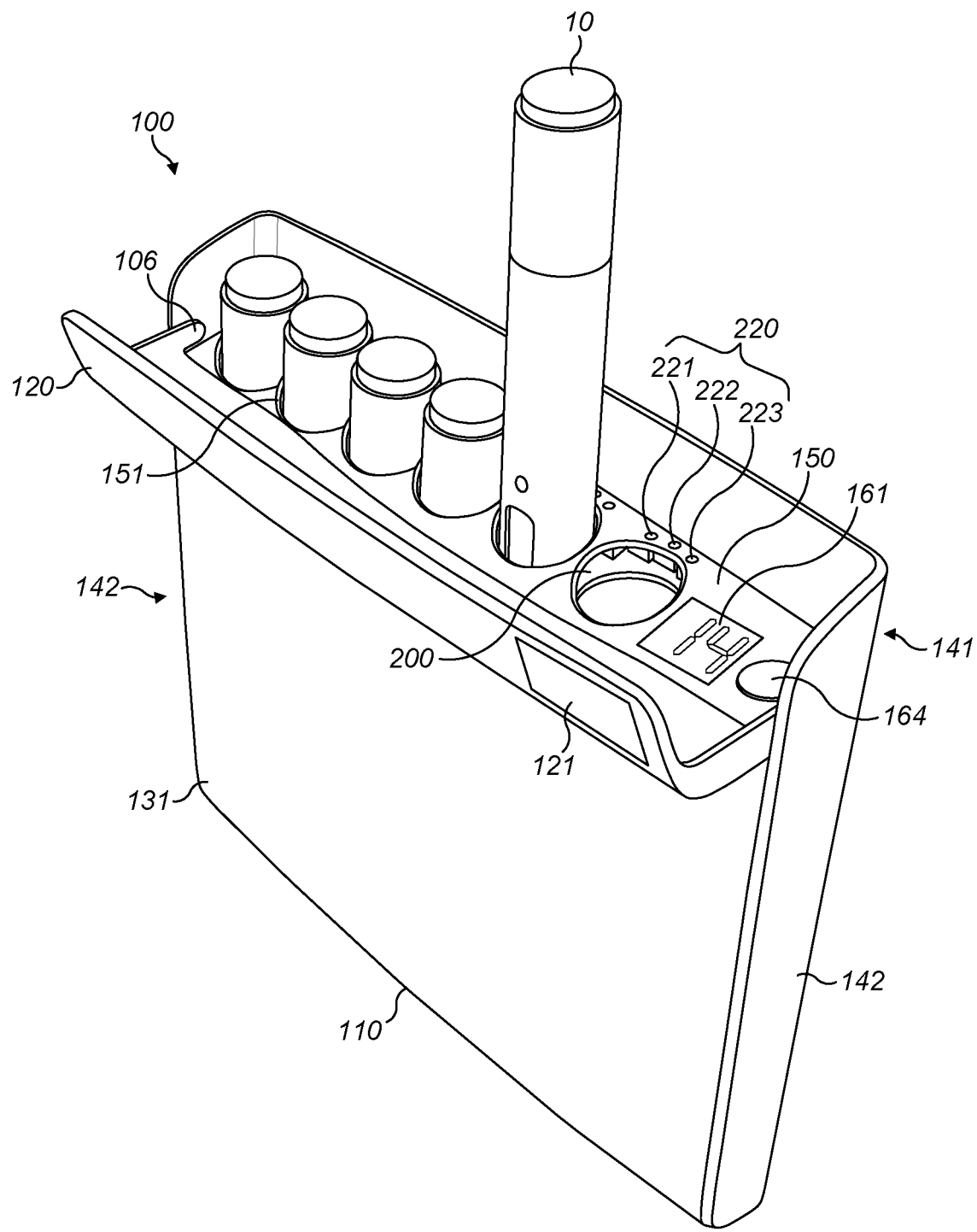
FIG. 7 shows a storage device.

With reference to FIG. 7, a storage device 100 according to exemplary embodiments is shown. The storage device 100 comprises a case 110 having a lid 120. The case 110 may comprises a lower face 131, an upper face 141, and two side walls 142. The lower face 131 is curved so as to meet the upper face 141 at the rear of the device. At a front end of the case 110, an opening is formed between lower face 131, the upper face 141 and the two side walls 142.

The lid 120 may comprise a latching mechanism to hold the lid 120 in the closed position. The lid 120 may further comprise a locking mechanism configured to prevent the lid 120 from moving to the open position. The locking mechanism may be controlled electronically. The case 110 is configured to hold and store a plurality of injection devices 10. A length of the case 110, measured between the rear of the case and the lid 120, is sufficient to accommodate the length of each of the injection devices 10. Other lid configurations are also contemplated. A portion of the lid 120 may be clear and transparent to form a viewing window 121 through the lid 120.

The case 110 further comprises a panel 150 arranged within the opening. The panel 150 comprises a plurality of openings 151. The openings 151 are configured to hold a corresponding plurality of injection devices 10. The openings 151 in the panel 150 are circular in shape. The openings 151 may be square shaped, or rectangular shaped to accommodate other sizes of injection device 10. The width of each opening is sufficient to accommodate the width of each injection device 10. The panel 150 comprises a row of six openings, so as to hold six injection devices 10 arranged in a row along a width of the case 110.

The storage device 100 may be configured to hold more than six, or fewer than six injection devices 10 in the case 110. A retention mechanism may retain the plurality of injection devices in position within the openings 151. The retention mechanism may comprise a mechanical catch configured to engage with each injection device 10, for example, a sprung push-catch push-release mechanism.

A user may receive the storage device 100 in an empty condition. When the user is supplied with a plurality of injection devices 10 they can be loaded into the storage device 100. The lid 120 is moved into the open position and each of the injection devices 10 is inserted into a corresponding one of the openings 151. The lid 120 is moved into the closed position. The storage device 100 is placed in the fridge until the first scheduled dosing time is due. The storage device 100 may be placed in the fridge before or after the initial insertion of injection devices 10.

For example, a dosing time for one type of injection device 10 may be scheduled every 14 days or 28 days, according to the prescription and/or product patient leaflet of the medicament provided with the injection device 10. For some injection devices 10, a period of time between scheduled dosing times may be between 2 days and 60 days, according to the requirements of the medicament. The storage device 100 may be configured to contain and store injection devices 10 of multiple types, simultaneously or at different points in time. The storage device 100 may contain a plurality of injection devices 10 providing one or more different medicaments with one or more different dosing intervals.

The storage device may comprise a processor arrangement (not shown) operatively coupled to a wireless communication module (not shown). The wireless communication module may be configured to broadcast a connection request signal when the fridge door is determined to be open. If a response signal is received from the user device 400, the wireless communication module is configured to establish communication with the user device 400. The processor arrangement controls communication with the user device 400.

The processor arrangement can control the wireless communication module to transmit information relating to the storage device 100 and the plurality of injection devices 10 to the user device 400. The wireless communication module may transmit a status of the injection devices 10, for example, the wireless communication module may transmit the time remaining until the next scheduled dosing time is due. The wireless communication module may transmit device information received from the sensor array 240, for example, the wireless communication module may transmit the number and types of injection devices 10 stored in the storage device 100. The wireless communication module may transmit an alert to the user device 400 if one of the injection devices 10 has expired.

The wireless communication module may transmit status information of the storage device 100 to the user device 400. For example, the wireless communication module may transmit environmental information provided by a temperature sensor or a humidity sensor.

The user device 400 may also initiate communication with the storage device 100, even if the fridge door is not open. This allows the application running on the user device 400 to override and update the information on the storage device 100 at any time. The application may also request that certain information is sent or resent by the storage device 100 at any time.

The storage device 100 is configured to establish communication with one or more user devices 400 and wireless terminals 300. In some embodiments, the storage device 100 is configured to determine whether or not the fridge door is open, and to establish communication conditional on the fridge door being open. The storage device 100 is further configured to transmit information relating to the plurality of injection devices 10 to a wireless terminal 300. The storage device 100 may be configured to request information relating to the plurality of injection devices from a wireless terminal 300.

In some embodiments, the storage device 100 is further configured to provide the user with a visual and/or audio reminder when the scheduled dosing time is due. The storage device 100 may be further configured to provide the reminder conditional on the fridge door being open. The storage device 100 may be further configured to determine whether the lid 120 is in the open position or the closed position, and to deactivate the audio reminder upon detection of the lid 120 being moved to the open position.

Figure 8A:
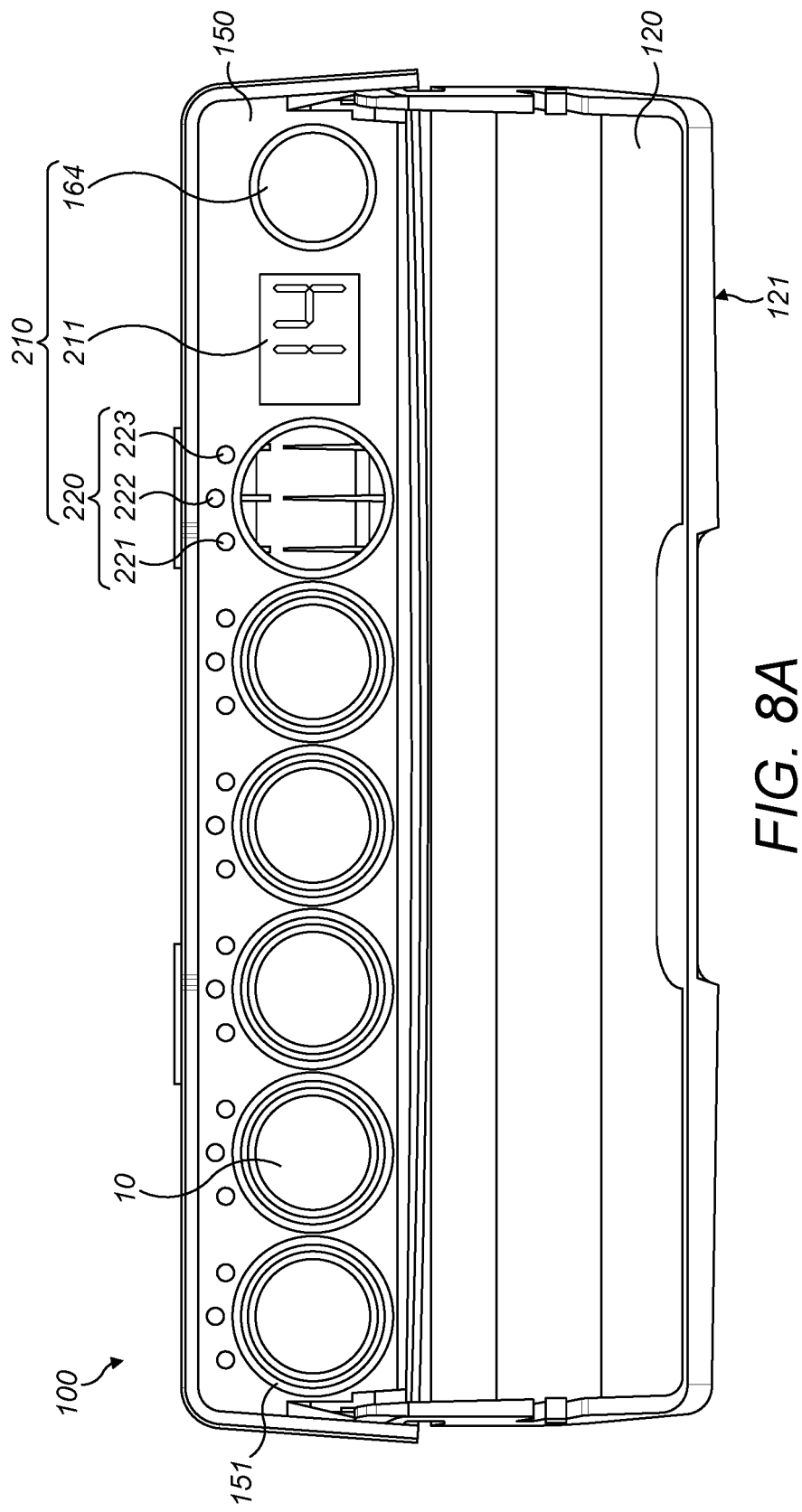
FIG. 8A shows the storage device from the front with the lid in the open position.

FIG. 8A shows the storage device 100 from the front with the lid 120 in the open position. The panel 150 and openings 151 are visible. The storage device 100 as shown contains a plurality of injection devices 10, each of which may be of a different device type. Different types of injection device 10 may provide different medicaments. Alternatively, different types of injection device 10 may have different dosages or concentrations of the same medicament, or different methods of delivering the medicament. Different types of injection device 10 may have different dosing intervals.

The storage device 100 includes an electronics system 200. The electronics system 200 comprises multiple components that are connected together to provide a specific set of functions, described below. The components of the electronics system 200 are mounted on a printed circuit board (PCB), although instead they may be interconnected through some other medium.

Some of the electronic components of the electronics system 200 are user interface hardware components and together provide a user interface 210 for the storage device 100.

The electronics system 200 comprises a display 211. The display 211 is an example of an optical transducer. The display 211 comprises two seven-segment light-emitting diode (LED) arrays. The display 211 is visible to the user through the transparent viewing window 121 in the lid 120 when the lid 20 is in a closed position. The electronics system 200 comprises a light-emitting diode (LED) array 220. The LED array 220 is an example of an optical transducer. The electronics system 200 comprises a reset button 164. The reset button 164 is an example of an input device. The reset button 164 is a sprung plunger button which may be depressed by the user. The electronics system 200 comprises a speaker. The speaker is an example of an audio transducer.

The LED array 220 comprises an array of eighteen light-emitting diodes (LEDs). The LEDs of the LED array 220 are arranged on the panel 150, in proximity to the openings 151. The LED array 220 comprises three LEDs 221, 222, 223 for each of the six openings 151. Each of the three LEDs 221, 222, 223 can be illuminated with a different colour. For example, the LED array 220 may comprise a blue LED 221, a white LED 222 and a red LED 223 for each opening 151.

Figure 8B:
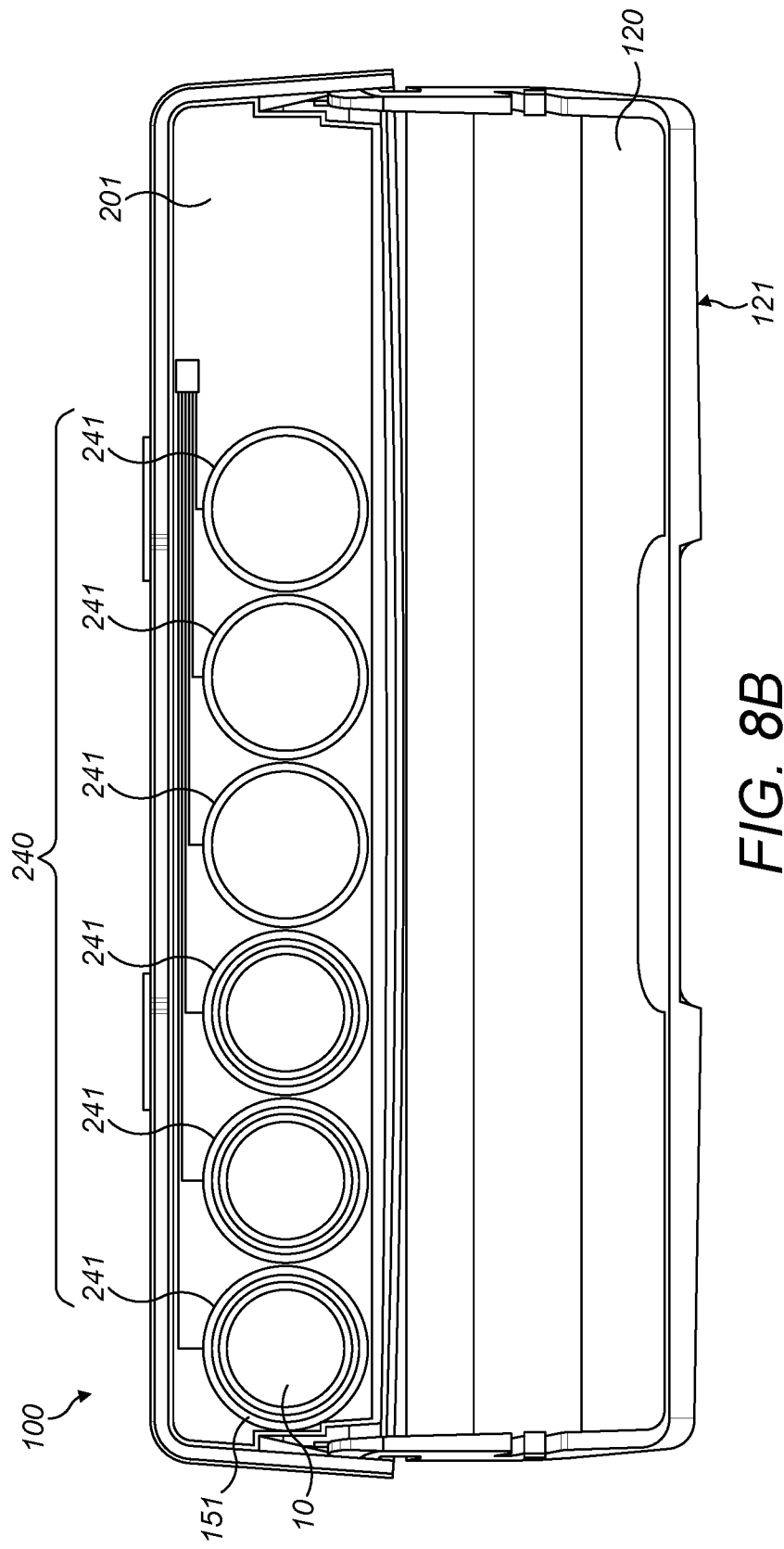
FIG. 8B shows an internal view of the storage device from the front.

FIG. 8B shows an internal view of the storage device 100 from the front. The rear face of the PCB 201 is illustrated.

The electronics system 200 comprises a sensor array 240. The sensor array 240 is mounted on a rear face of the PCB 201. The sensor array 240 comprises a plurality of device sensors 241. The number of device sensors 241 corresponds to the number of injection devices 10 which can be stored by the storage device 100. Each device sensor 241 is mounted in proximity to one of the plurality of openings 151.

The device sensor 241 is configured to output a signal when an injection device 10 is located in the opening or during insertion into opening 151. The device sensor 241 is a radio-frequency identification (RFID) reader comprising a radio-frequency antenna. Each device sensor 241 is in the form of a loop corresponding to each of the openings 151. The device sensor 241 is arranged to detect a device tag arranged on the injection device 10. The device tag is a passive RFID tag comprising a radio-frequency antenna. The device sensor 241 generates an electromagnetic field, which activates the device tag, and detects a response signal transmitted by the device tag. The device sensor 241 may be configured to read device information stored on the device tag. The processor arrangement 230 may store device information received from an injection device 10.

The sensor array 240 may include electronic components that are separate to the device sensors 241 but form part of the sensor array 240 itself. The device sensors 241 may provide signals transmitted by a device tag and the electronic components perform analysis of the signal and communication to the processor arrangement 230. Alternatively, each device sensor 241 may include electronic components to perform analysis of a detected signal. Further alternatively, the analysis of incoming signals may be performed by the processor arrangement 230.

System Description

Figure 2:
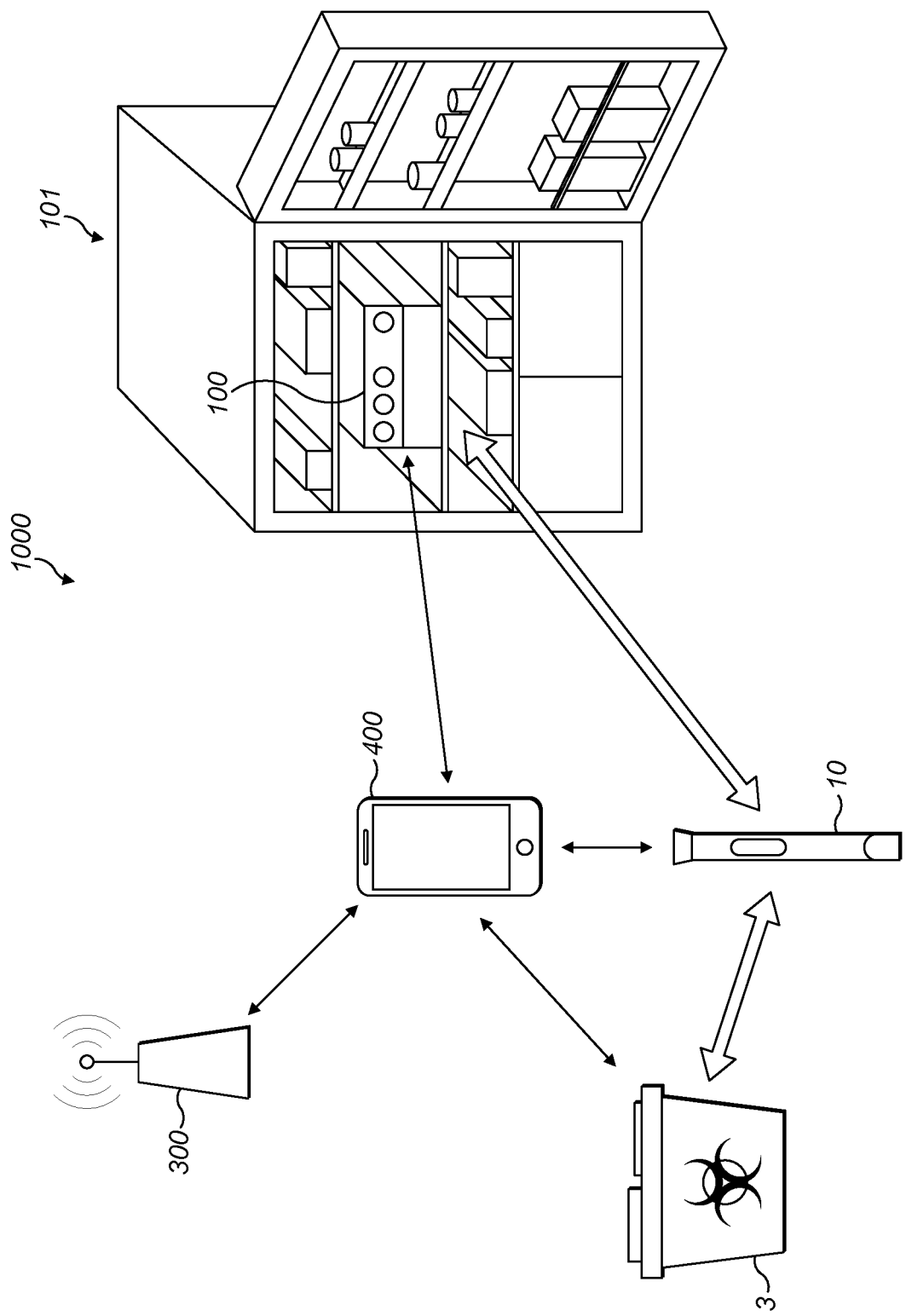
FIG. 2 shows a system including the user device of FIG. 3 and a storage device.

With reference to FIG. 2, a system 1000 according to various embodiments is shown. The system 1 comprises the storage device 100. The storage device 100 is shown to be located in a refrigerator, according to an exemplary mode of operation. The storage device 100 may be placed in the refrigerator by a user, and a plurality of injection devices 10 may be placed in the storage device 100.

The system comprises a user device 400 as described above, one or more injection devices 10 as described above, a digital sharps bin 3 and a wireless terminal 300.

In some embodiments, the user device 400 may be a mobile phone. The user device 400 is an example of a wireless communication device. The user device may alternatively be referred to as a communication device, computing device or mobile device and is not necessarily associated with a single user. The user device 400 is configured to communicate wirelessly using a wireless communication protocol. For example, the first external device may communicate wirelessly using Wi-Fi, Bluetooth, ZigBee, IrDA or similar.

The user device 400 can be operated by, for example, a patient. According to the exemplary mode of operation, the user device 400 is in close proximity with the storage device 100. For example, the user device 400 may be carried or held by the patient.

The wireless terminal 300 may be a wireless access point such as a wireless router. The wireless terminal 300 is configured to broadcast a Wi-Fi signal. Alternatively, the wireless terminal 300 may be configured to broadcast a signal using Li-Fi or any alternative wireless protocol. The wireless terminal 300 provides access to a wireless LAN for compatible devices within range. The wireless terminal 300 may be configured further to provide access to the Internet through the wireless LAN. The wireless terminal 300 is connected to the internet through an Ethernet connection, a PLC connection or wirelessly using Wi-Fi, Li-Fi or a mobile communication protocol such as GSM, CDMA, EDGE, GPRS, HSPA, WiMAX, LTE or similar.

As shown, the user device 400 may communicate directly with the storage device 100, injection device 10 and digital sharps bin 3, using Bluetooth, Zigbee or another suitable peer-to-peer protocol. Alternatively, the user device 400 may communicate only with the storage device 100. The injection device 10 may exchange information with the storage device 100 and this information is then pushed or otherwise synchronised with the application on the user device 400. In some other embodiments, the user device 400 communicates with the storage device 100 only via the wireless terminal 300. The digital sharps bin 3 may also communicate only via the wireless terminal 300 and may thereby exchange the information it receives from reading the injection devices 10.

In some other embodiments the injection device 10 can have a similar level of functionality to the storage device 100. For example, each injection device 10 can be programmed with a countdown indicating the number of days remaining before it should be used for an injection. Each injection device 10 may also monitor and report its temperature to the user device 400. The injection device 10 may also be configured to report when it has been used.

As previously described, user device 400 may run an application allowing it to read information from and exchange information with the storage device 100, digital sharps bin 3 and injection devices 10. For example, the user device 400 may transmit and receive a first set of signals with the storage device, the first set of signals representing data associated with a specific injection device stored in (or to be stored in) the storage device and may transmit and receive a second set of signals with the digital sharps bin, the second set of signals representing data associated with the specific injection device disposed of in the sharps bin. Many of the features of the storage device 100 described above may be implemented by the application on the user device 400 such that the user device acts as the primary control and alert means for system 600.

For example, the storage device 100 may have sensors which determine whether an injection device 10 is present in each of the openings, but not any further information about injection devices 10. Instead, user device 400 is used to scan each injection device 10 before it is placed into the storage device. This may be done by scanning or photographing a label provided on the body of the injection device 10. In some other embodiments, the information is stored on an RFID tag or similar which is interrogated by the user device 400. The user device 400 determines at least the type and quantity of medicament in the injection device 10 as well as any expiration date. The information contained on the label or RFID tag may also comprise a device ID, a device type, a dosing time period and a warm-up time period for the injection device 10.

Having obtained information from the injection device 10 in this manner, the user device 400 then monitors the time until the next injection is due. At a specified customisable time before the next injection is due, the user device 400 can remind the user with a visual and/or audible alert. If an injection device 10 reaches its expiry date, then this too can be communicated to the user via the user device 400.

The user device 400 may also be used to scan each injection device 10 when it is removed from the storage device 100 for use. This allows the user device 400 to remind the user if the injection device 10 must be left to warm up at room temperature for a minimum time before it is used and to alert the user when that time has elapsed. The minimum time may be based for example on the local temperature (e.g., the storage device 100 temperature or the injection device 10 temperature) and the operational temperature of the injection device 10 or the medicament (e.g., room temperature). Scanning an injection device 10 when it is removed from the storage device 100 may also act as a determination that the injection device 10 has been used, allowing the user device 400 to track the user's dosing history and monitor dosing regimen adherence. The user device 400 may display an interface asking the user to confirm that the scanned injection device 10 has been used.

The storage device 100 has openings for multiple injection devices 10. If the user device 400 is used to scan each injection device before it is stored and when it is used, then the user device can also be used to track the number and type of injection devices stored and therefore the user's current supply of injection devices. The user device 400 can display a reminder when the user needs to order more injection devices 10, for example when only one injection device remains, or some time before the last injection device is due to be used.

In some other embodiment, the storage device 100 is able to determine at least an ID of the injection device 10 in each opening. This allows the user device 400 to communicate to the storage device 100 which of the stored injection devices 10 should be used at any time. For example, if the storage device 100 is storing several identical injection devices 10, then at the time of injection, the user device 400 can indicate that the injection device 10 having the closest expiration date should be used. If suitably equipped, the storage device 100 can indicate the injection device 10 that the user should use by illuminating the opening containing that injection device 10. Alternatively, or in addition, the user device 400 may indicate which opening contains the injection device 10 to be used with a text or audio cue or visually with a representation of the storage device 100. In some circumstances the user must use two injection devices 10 for a dosing, for example at the beginning of a treatment programme. In other cases, the storage device 100 may be used to store two different types of medicament that the user takes. In these cases, it is important that the stored injection devices 10 can be differentiated and individually indicated to the user by the user device 400 and/or the storage device 100.

In some embodiments, the user device 400 is configured to determine where the injection devices 10 should be placed within the storage device 100 and to indicate this information to the user. The user device 400 is configured to scan a first injection device 10 using a camera, RFID reader or other suitable hardware and to determine at least one of a drug dosage contained within the injection device and a device expiration date of the injection device. The user device 400 then determines which of the openings of the storage device 100 should be used to store this injection device. By default the user device may choose the left most empty opening, but in some situations, for example where the user is prescribed two different medicaments or two different dosages of the same medicament, the user device may determine that the rightmost empty opening should be used. The user device 400 may also attempt to have the injection devices stored in order of expiration date from left to right. This process can then be repeated until the user has stored all of the injection devices they have received.

The user device may display a representation of the storage device and in particular of the openings of the storage device. After scanning an injection device, the user device may display this representation and indicate on it which of the openings to store the injection device in. This may be done by illuminating the respective opening on the representation, by displaying text with suitable instructions, an arrow pointing to the respective opening or a combination of these. The user device may also emit audible tones or audible instructions regarding placement of the injection device. If the injection device is placed in a correct opening (i.e., an opening where a specific injection device should be located), then the user device may display a confirmation message. If the injection device is placed in an incorrect opening, then the user device may display a message indicating this, and may prompt the user to move the injection device to the correct opening. However, if all the openings are identical and if the user does not comply with this prompt for correct placement, then the user device may update the information it holds on where each injection device is stored accordingly.

At the time when an injection is due, the user device 400 may then indicate to the user which opening contains the injection device 10 to be used, again by indicating it on the representation of the storage device and/or with an audible instruction. Where the storage device is configured to receive and interpret such commands, the user device may also send a signal causing the storage device to indicate which opening to remove an injection device from, for example by illumination the opening.

The storage device 100 detects when an injection device is placed in or removed from an opening. The storage device 100 may also have a wireless transceiver and be configured to send a signal to the user device 400 indicating which one of the plurality of openings an injection device was placed in or removed from. Where the sensors of the storage device are able to identify the specific type of the injection device, this information is also sent in the signal. The user device receives this signal and checks whether the injection device was placed into or removed from the correct opening. If the injection device was removed from the correct opening, then the user device may output a confirmation message. If the injection device was removed from an incorrect opening, then the user device may output an alert. In some cases, for example where all of the stored injection devices contain the same dosage of medicament, which injection device is used may not be critical. In such a situation, the user device may output an alert, but take no further action if the alert is ignored. If the user replaces the injection device into the opening from which it was removed and then removes the injection device form the correct opening, then the alert is cancelled. If the user does not replace the incorrect injection device, then the user device may continue to output the alert, for example on the display or audibly. If the user continues to ignore the alert, the user device may determine that an incorrect medicament or incorrect dosage may have been administered, and may send an alert message to the user's Healthcare Professional or to the user's patient support programme. In this way, the risk of mis-administration can be reduced.

Where the storage device contains several injection devices which are identical, in that they contain the same dosage of the same medicament, the user device may be configured to select the injection device having the earliest expiration date and to indicate the opening containing this injection device on the representation of the storage device and/or by transmitting the indication to the storage device. In this way, the likelihood of a medicament exceeding its expiry date and being wasted is reduced.

In some situations, for example when the user is administering the first dose of a prescribed medicament, or where different doses of medicament must be administered, the user may be required to use two or more injection devices. In this situation it may be important to guide the user since they may be unfamiliar with the procedure. The user device may be configured to indicate the two or more openings of the storage device containing the different injection devices. to the user device may differentiate between the two or more openings using a representation of the storage device and/or by signalling to the storage device. The storage device can then illuminate the openings accordingly, for example by illuminating only the opening containing the first injection device which should be used or by illuminating the two or more openings in different colours and/or by having the opening of the first injection device to be used flash. Similar illumination may be used on the representation displayed on the user device with explanatory text and/or audible instructions.

In addition, user device 400 may remind or prompt a user to confirm the appropriate injection device 10 has been selected from one or more openings. For example, user device 400 may remind a user to confirm the expiration date, dosage, type of medicament, etc. For example, a treatment may require a high priming dose of medicament followed by periodic lower maintenance doses. Such a treatment may be achieved using two or more injections devices for the priming dose, and less injection devices for the maintenance doses. Specifically, two injection devices may be used for a priming dose that is twice the dosage of a maintenance dose, whereby the maintenance dose is achieved with a single injection device. Alternatively, a single injection device may contain twice the dosage of a medicament needed for maintenance dosing. Here, user device 400 could instruct the user to use this single injection device for the priming dose, and then use other lower dosage injection devices for the periodic maintenance doses. As described above, storing or using injection devices containing different doses of medicament may require additional confirmation steps to ensure the user is using the appropriate injection device. Such information may also be stored and/or transmitted to a third party to improve patient compliance with a particular dosing schedule.

In some embodiments, the user device 400 may request the user to scan the injection device 10 after it has been used. This allows for improved user adherence monitoring and dosage regimen tracking. The user device 400 may also communicate with a digital sharps bin 3. In some embodiments the digital sharps bin 3 may be configured to detect when an injection device 10 is deposited inside, but no further details of the injection device. The digital sharps bin 3 may communicate the detection to the user device 400. The user device 400 may then check if any injection devices were recently scanned after being removed from the storage device and link the disposal in the digital sharps bin 3 with the scanned injection device. Alternatively, the user device 400 may ask the user to confirm that the injection device just disposed of in the digital sharps bin 3 was the recently scanned injection device 10.

In some other embodiments, the digital sharps bin 3 is able to scan the deposited injection device 10 to determine at least its ID and to communicate the ID to the user device 400. The digital sharps bin 3 may scan the deposited injection device by interrogating an RFID tag on the injection device or by taking an image of a label on the injection device. This allows the user device 400 to link the disposal in the digital sharps bin 3 with the scanned injection device 10 without the need for user confirmation. The user device 400 can be configured indicate that the scanned injection device 10 was used even if the injection device 10 was not scanned after use, but only after being removed from the storage device 100.

The user device 400 may also be configured to calculate a personal adherence score for the user based on the scanning of the injection device 10 and/or data received from the digital sharps bin 3. This personal adherence score may be displayed to the user periodically or on demand. The user device 400 can also display whether the user is on schedule with their medication. If the user is not on schedule the user device may display an alert. The user device may also be configured to generate an injection device usage report, based on the signals exchanged between the user device and the storage device and or the signals exchanged between the user device and the digital sharps bin. The injection device usage report may contain information on when and optionally how each injection device was used and disposed of, and optionally also the personal adherence score mentioned above.

As used herein, the term "the user device 400 determines" covers the user device scanning and recording information from the injection devices 10 or receiving information form the storage device 100, digital sharps bin 3 or other system component. Where the user device 400 is described as "confirming" some information or statement (such as whether the injection device is suitable for storage in the storage device 100), this covers the user providing some confirmation to the user device 400 that the relevant information is correct. For example, the user device 400 may display the information scanned or otherwise received and ask the user to check this against what they know or can see. If the user responds in the positive, then the user device 400 "confirms" the accuracy of the information. In some other situations, the user device 400 may "verify" the accuracy of information it scans or receives by checking it against information it already holds. For example, after reminding a user to use a particular injection device, the user device may be used to scan an injection device. The user device may then check at least the ID of the scanned injection device against the stored information (in this case the identity of the injection device which it reminded the user to use) to verify that it is the correct injection device.

User Device Features and Functions

Figure 3:
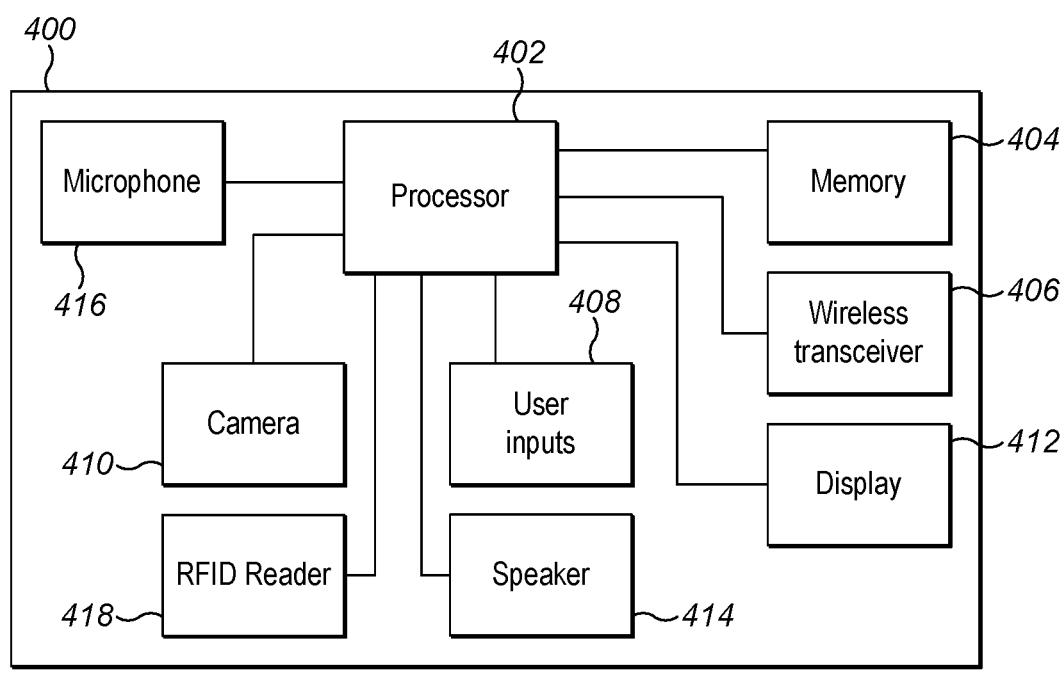
FIG. 3 is a schematic illustration of a user device according to some embodiments.

FIG. 3 illustrates schematically a user device 400 according to some embodiments. The user device 400 may be a mobile phone. The user device 400 is an example of a wireless communication device. The user device may alternatively be referred to as a communication device, computing device or mobile device and is not necessarily associated with a single user. The user device 400 is configured to communicate wirelessly using a wireless communication protocol. For example, the first external device may communicate wirelessly using Wi-Fi, Bluetooth, ZigBee, IrDA or similar.

The user device 400 can be operated by, for example, a patient. According to the exemplary mode of operation, the user device 400 is in close proximity with the storage device 100. For example, the user device 400 may be carried or held by the patient.

The user device 400 comprises a processor 402, a memory 404, a wireless transceiver 406, user inputs 408, a display 412, a camera 410, a microphone 416, and RFID reader 418 and a speaker 414. In some embodiments the user device 400 is a smart phone or tablet computer. The processor 402 may for instance be a microprocessor, a Digital Signal Processor (DSP), Application Specific Integrated Circuit (ASIC), Field Programmable Gate Array (FPGA) or the like. The display may be a touch sensitive display and may be based on capacitive or resistive sensing technology.

The memory 404 may comprise both a program memory storing program code (e.g., software or firmware) and main memory storing data. The processor 402 is configured to execute the program code stored in the program memory and to read, write and delete data from the main memory. In some embodiments, the program code may be an application which can be downloaded and installed on the user device 400. The application provides connectivity with the storage device 100. The application may in addition be a disease management and tracking tool for use by patients. The program memory may for instance be a Read-Only Memory (ROM), and the main memory may for instance be a Random Access Memory (RAM).

The user device 400 may communicate over a WLAN, by using Bluetooth, or by using any other suitable wireless protocol, via the wireless transceiver 406. The user device 400 may comprise multiple network interfaces and may use any of these to exchange data with the storage device 100, injection devices 10, digital sharps bin 3 or any combination thereof.

The user device 400 comprises one or more user inputs 408, for example a touchscreen, keypad or keyboard, accelerometer or gyroscope, mouse or microphone 416 for receiving voice commands. User device 400 may also comprise a camera 410 configured to capture images of a user and images of labels, codes and the like visible on the injection devices 10. The user device may be configured to scan the injection devices using a scanning device. The scanning device may refer to either the camera 410 or RFID reader 418. The term "scanning" as used in relation to the user device 400 may refer to use of either of these components to read information provided on the injection device 10.

In operation, the user device 400 uses wireless transceiver 406 to connect with the storage device 100, injection devices 10, digital sharps bin 3 or any combination thereof via the wireless communication module 260 of the storage device. In some embodiments this connection uses a Bluetooth protocol to form a direct pairing between the two devices. The pairing may be initiated at any time by the user device 400. In addition, the storage device 100 may attempt to initiate a Bluetooth pairing when it detects that the fridge door is opened or when a dedicated button on the storage device 100 is pressed. In some other embodiments, the connection between the user device 400 and storage device 100, injection devices 10, digital sharps bin 3 or any combination thereof uses a WiFi connection via the wireless terminal 300.

The connection between the user device 400 and the storage device 100 allows operational information to be set either on the storage device 100 or via the application on the user device 400 and to be synchronized between the two devices.

Once connected, the storage device 100 may be configured to periodically transmit information to the user device 400 and the user device may push certain information to the storage device 100. The storage device 100 transmits countdown information indicating a number of days remaining until a next injection is due. The storage device 100 also transmits temperature information and battery level information. If equipped with suitable sensors, the storage device 100 may also transmit information indicating the number of drug injection devices remaining in the storage device 100. The user device 400 receives and stores this information in memory 404. The user device 400 can transmit certain information to overwrite that stored on the storage device 100, such as the current time and date, the number of days remaining until the next injection is due, the injection interval and the number of drug injection devices stored in the storage device 100. The operation information described above may also be pushed to or from the injection device 10 and/or digital sharps bin 3 if enabled, such that all connected devices have up to date information.

When a user opens the application on the user device 400, a home page is displayed on the display 412. The home page may display the number of days remaining until a next injection is due. If the user determines that the displayed number of days remaining until a next injection is due is incorrect, they may enter a countdown reset command using the user inputs 408. Even where the displayed number of days remaining until a next injection is due is correct, the user may use the application to reset the counter on the storage device, rather than the reset switch 215. In response to receiving the countdown reset command, the user device 400 sends the countdown reset command to the storage device 100. Upon receiving the countdown reset command, storage device 100 overwrites the information it stores indicating the number of days remaining until a next injection is due and resets the value to the predefined initial value.

The user device may also receive a reset notification from the storage device 100 when the user presses the reset switch. In response, the user device 400 resets the number of days remaining until a next injection is due to a predefined initial value on the user device. In this way, the user can continue to use the reset switch 215 on the storage device 100 if desired, but the application on the user device can override the information on the storage device 100 if it is determined that this is incorrect. Whenever the user device 400 receives a reset notification from the storage device 100, or a countdown reset command is received via the user inputs 408, a reset time stamp is created and stored in the memory 404. The time stamp includes the precise date and time at which the reset occurred.

In some other embodiments, the user may adjust the number of days remaining until a next injection is due. This updated value may then be stored on the user device 400 and communicated to the storage device 100. The range by which the user can adjust the number of days remaining until a next injection is due may be limited by the injection interval e.g., ±14 days.

The home page of the application may optionally also display the number of drug injection devices remaining in the storage device 100. Using user inputs 408, the user can manually input the number of drug injection devices remaining in the storage device 100. This information is optionally transmitted to the storage device 100. The application may also decrease the recorded number of drug injection devices remaining in the storage device 100 by one.

The home page of the application may display a local temperature, e.g., a current temperature of the storage device 100, based on the temperature information transmitted by the storage device. The user may use the application to set upper and/or lower threshold temperatures which the storage device 100 should not exceed. If the temperature reported to the user device by the storage device 100 exceeds the thresholds, the application is configured to emit an alert. The alert may be visually displayed on the display 412 and/or audibly emitted via the speaker 414.

The injection interval (scheduled time between injections) may be predefined as 14 days. The storage device 100 may be pre-programmed with this interval. However, the user may be prescribed a different interval, such as 21 days or 28 days. The application allows manual adjustment of the injection interval by the user. Upon receiving a manual adjustment of the injection interval, the user device 400 pushes the updated injection interval to the storage device 100, which is then stored as the new predefined initial value. When the application determines that only one day remains before the next scheduled injection, a reminder is displayed on the display 412. On the schedule day of injection, a further reminder is displayed and an audible alert may also be emitted by via the speaker 414. The user may set the time of day at which the reminders/alerts are activated.

When the application determines that only one drug injection device remains in the storage device 100 after a countdown reset, the application displays a re-order reminder on the display 412. A reminder may also be displayed when only two drug injection devices remain. When the battery level of the storage device 100, as reported to the user device 400 by the storage device 100, drops below a predefined threshold, the application causes a visual and/or audible alert to be emitted by the user device 400.

In addition to the connectivity and data exchange with the storage device 100, the application may also act as a disease management and tracking tool. The application may allow a user to track the progress and symptoms of a skin condition, such as Atopic Dermatitis. The application may allow the user to record the occurrence and severity of symptoms such as skin flare ups, itchiness, sleep loss and stress. The user may use the application to enter information relating to a flare up of symptoms and/or may regularly record the severity of symptoms, for example once per week. The application may feedback anonymized usage information to allow key performance indicators (KPIs) of the application to be assessed. By collating information from multiple user devices running the application, the developer or provider of the application may be able to determine one or more of the number of downloads, the number of registrations initiated, the number of registrations completed, average session length, average session frequency, average session intervals, number of screens/journeys per session, most used functionalities, number of weekly active users, number of monthly active users and a measure of adherence improvement compared with a baseline level.

As well as providing connectivity with the storage device 100, the application on the user device 400 allows the user to monitor progress of their disease, as described in greater detail with respect to FIG. 3. The application allows the generation of patient summary reports, to be shared with the patient's HCP.

Figure 4:
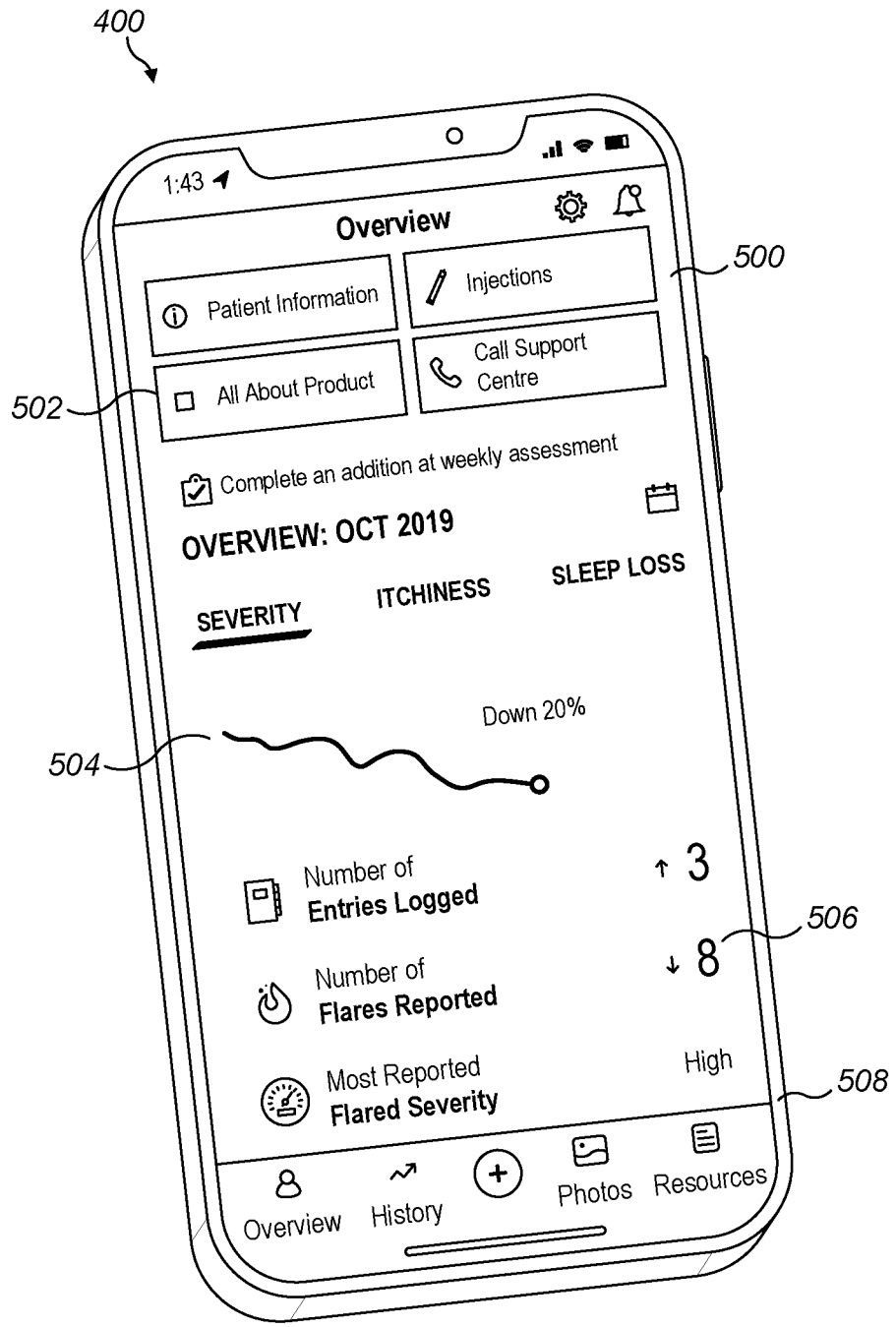
FIG. 4 shows a user device displaying an overview screen shot.

Referring now to FIG. 4, the user device 400 is shown displaying an overview screen shot 500. The overview page 500 may be accessed via a soft button from the home page of the application. The overview 500 comprises a number of quick link soft buttons 502. Selecting any of these buttons may open a web browser and navigate to a web page containing information, or open a telephone application on the user device 400 pre-populated with a phone number.

The overview page 500 also comprises an activity graph 504, illustrating the users reported level of symptoms of Atopic Dermatitis (or similar skin condition) over a recent time period. The activity graph may be switched between showing severity, itchiness and sleep loss. The overview page 500 also displays certain statistical information 506 relating to the symptoms reported by the user, such as the total number of entries logged, the number of flare-ups reported, the median level of flare severity reported, the median level of sleep loss reported and the median level of itchiness reported.

The overview page 500 also displays a number of icons 508 which are selectable to navigate to various pages of the application. These may include an overview page icon, an injection history page icon, a photos page icon, a new entry page icon (central icon in FIG. 3) and a resources icon. The icon corresponding to the currently viewed page may be highlighted.

Selection of the history icon may show a more detailed version of the graph shown in the activity graph 504. The time period may be adjusted to show, for example the last week, the last month or the last year of entries. The history may be toggled between showing severity, itchiness, sleep loss or stress or may show traces for two or more of these variables.

Selection of the new entry icon may open a short questionnaire about a flare-up. For example, the user may be asked to select a possible trigger for the flare-up (such as humidity or heat) and the level of symptoms such as itchiness, sleep loss and stress. Each symptom may be recorded as low, medium or high. The user may then be prompted to take a photograph of the flare-up. Alternatively, the application may allow the user to add an image as the first step in recording a flare-up. The application may then ask the user to enter other information about the flare-up, but entering this information may be optional.

Figure 5:
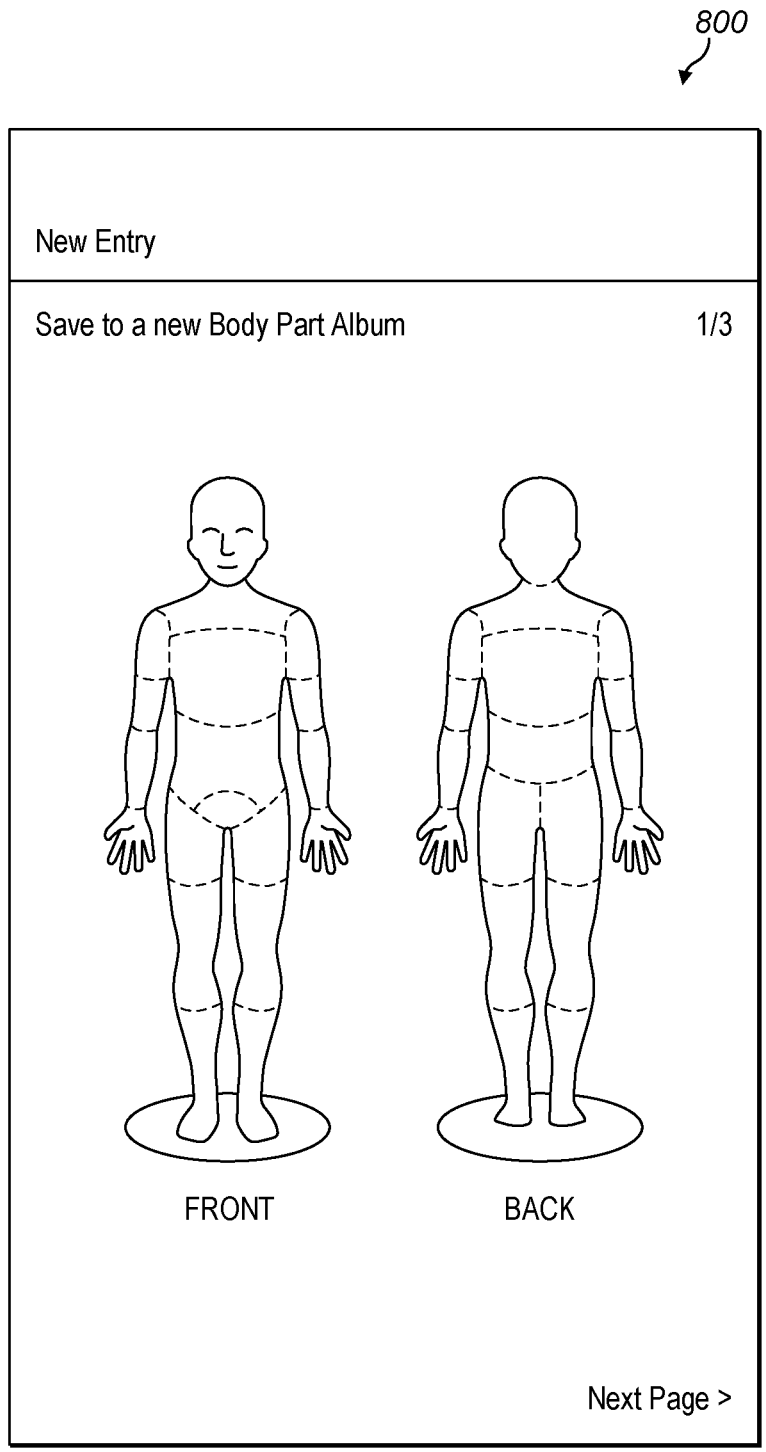
FIG. 5 shows a body part screen shot displayable on the user device of FIG. 3.

When the user instructs the application to record an image, the application accesses the camera 410 of the user device 400. Once the user has taken a photograph, the application presents a body part screen 800 as shown in FIG. 5. The body part screen depicts a person with body areas demarcated. The user can then select a body area corresponding with the photograph they have just taken. The user then saves the new entry. The application creates a patient photo journal from the images and other information entered by the user. Each image is stored with an associated time stamp, an associated body part and any trigger, symptom and severity information entered.

Selection of the photos icon may show an album of all of the photographs taken by the user using the application. The user may filter and sort these photographs by body area, or by associated symptom and/or severity. For example, the user may filter the photos in the patient photo journal by showing only photos of the palm of their left hand. The application may then display only these images and optionally a time line showing when the images were captured and/or a chart indicating the user entered trigger, symptom and/or severity data. Alternatively, the patient photo journal may be automatically grouped according to body part. The patient photo journal may also be viewed via a mannequin, similar to those shown in FIG. 5. Each body area which has associated photographs may be highlighted or coloured. The user may then select one of the body part areas on the mannequin to open the associated photo album.

In another embodiment, body part screen 800 as shown in FIG. 5, or a similar representation of a complete or a partial body, may be used to record locations or associated images of injection sites. For example, a patient may record where on their body and when an injection was made. Such injection location and date information may be stored by user device 400. Thus, a history of injection site information could be recorded.

As well as injection site location, user device 400 could be configured to ask the patient for information related to the injection experience, and store such information. This could include, for example, how the patient was feeling that day, was the injection painful, did the injection device operate properly, was an entire dose of the medicament delivered, etc.

User device 400 can be further configured to take and store associated images of the injection site before and after injection. Such image data may be recorded to track where an injection has occurred or any adverse reactions at the injection site. Such tracking of injection sites may be needed for patients with skin disorders as the location of a pre-existing skin lesion at a desired injection location may not make the site suitable for injection.

Figure 10:
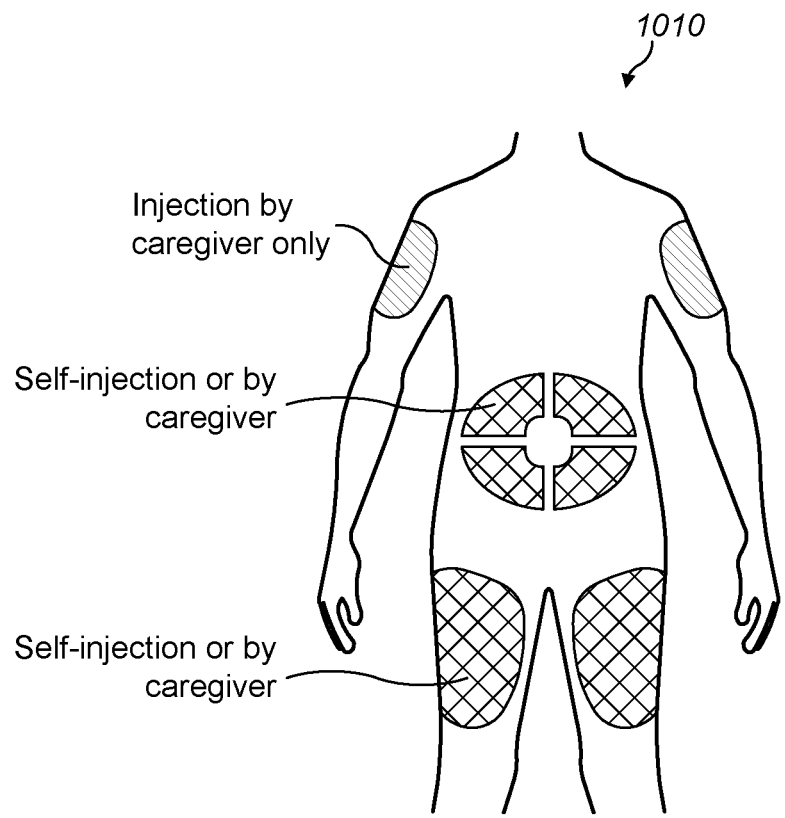
FIG. 10 shows a second body part screen shot displayable on the user device of FIG. 3.

Moreover, tracking where a patient injects on their body may improve patient adherence. For example, if a body part is over-used for injection, user device 400 may recommend a different body part be used. Conversely, if a body part is under-used for injection, user device 400 may recommend to the patient that that body part be used for an injection. Such recommendations may assist a patient in choosing an appropriate injection site when injections are infrequent. A patient may simply forget where they made an injection if injections are once every one, two, or four weeks. In this regard, the application may present a second body part screen 1010, as shown in FIG. 10. The second body part screen 1010 illustrates different potential injection areas on the displayed body. Some of these areas, for example on the upper arms may be indicated as for injection by a caregiver only. The most common areas for self injection are the upper legs and abdomen. The application may indicate a recommendation for which of these areas should be used for the next injection, for example by causing the area to be highlighted, causing it to flash, an arrow or lead line to appear with a written indication that the area could be used, or any other suitable way of drawing attention to the suggested body area.

Any data related to the injection site or associated images (including video, with or without audio) of the injection site, or which body part was injected, may also be provided to a health care provider or third party via user device 400. Such information could allow the health care provider to provide better advise to a patient. For example, a patient with a low body mass index ("BMI") may experience less pain if they inject into their abdomen instead of their leg. However, a patient with a high BMI may find it easier to operate an injection device on their leg. Moreover, a patient experiencing a flare-up of skin lesions on their abdomen may be advised to operate the injection device on their leg or have a caregiver inject medicament into the patient's arm. Such a customized injection protocol can be developed for each patient, with the aid of user device 400, to improve patient experience.

The application may also prompt the user to complete certain disease activity and impact on quality of life assessments. The prompt may appear when each new entry is recorded or periodically, for example once per week, depending on the type of the assessment. These assessments may be optional. For example, the application may prompt the user to complete a PO-SCORAD and/or POEM questionnaire to assess disease activity and a DLQI questionnaire to assess impact on quality of life. Each of these assessments may produce a score as the output.

The application may also be used to create reports. A "generate report" button may be provided on the overview screen or on the patient photo journal screen. The reports may be viewed by the user and may be shown or transmitted to the user's doctor. When the user selects the generate report button, a screen may be shown allowing the user to select what data is to be included in the report. The application may be configured to generate history graphs for symptoms (severity, itchiness, sleep loss, etc) and the user may select one or more of these.

By default the report may have a time range of the current month, however this may be adjusted as required. Other data which can be included in the report comprises number of entries logged, number of flares reported, most reported flare severity, most reported level of sleep loss, most report stress level, most reported trigger and photos form the patient photo journal.

Where the disease activity and/or impact on quality of life assessments have been completed by the user, the report may also include the results of these. For example a PO-SCORAD or POEM score may be shown in the report, either for the time period selected as a whole, for each week represented in the report, or for each entry in the report. Where a score is calculated for each week represented in the report or each entry in the report, the scores may be shown as a graph of assessment score against time. Any DLQI scores stored for the report time period may be displayed in the same manner as for the disease activity scores.

Selection of the resources icon may show a page containing further information and training modules on Atopic Dermatitis. Modules on understanding Atopic Dermatitis, managing Atopic Dermatitis and communication with the user's Healthcare Provider, among other, may be provided in this section. Each of these modules may consist of several articles. Additional education content may be delivered via the application in the form of short tips displayed on the overview screen and/or quizzes offered periodically. The application allows users to better track the progress of their disease and to more easily determine the possible triggers for their flare-ups. The combination of information collected in the application regarding the timing, severity and symptoms of a flare-up can also allow for a better clinical outcome when viewed by a HCP, since it provides a much more complete representation than would usually be gained from speaking with the patient.

Figure 6:
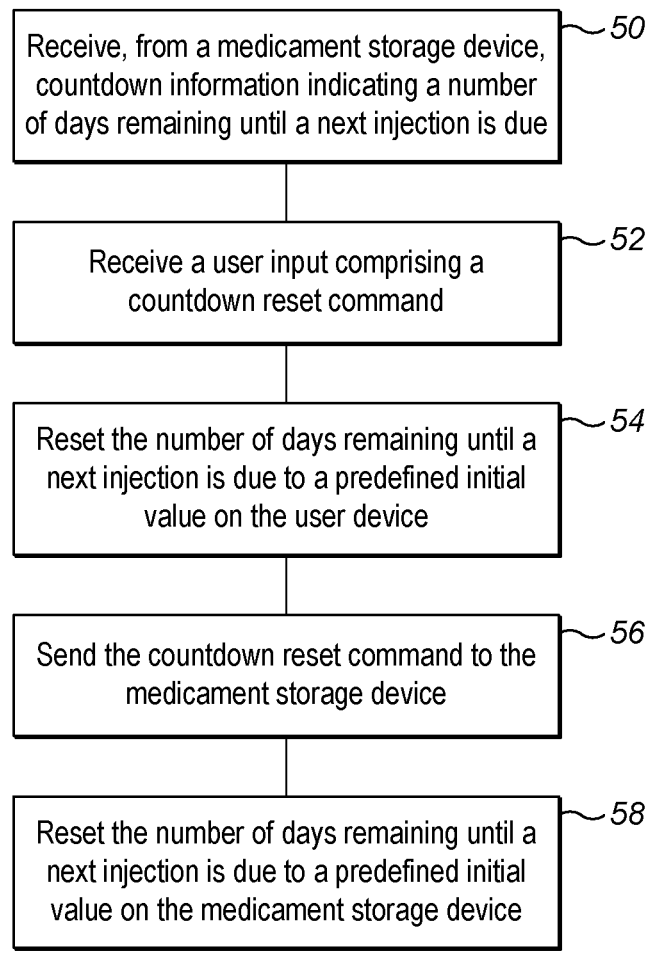
FIG. 6 is a flowchart showing exemplary operation of an application running on the user device of FIG. 3 according to some embodiments.

FIG. 6 is a flowchart showing exemplary operation of the application running on the user device and according to some embodiments. The process begins at step 50, when the user device 400 receives countdown information from the storage device 100. The countdown information indicates the number of days remaining until a next injection is due. This information may be automatically pushed by the storage device 100 to the user device 400 when the two devices first connect and/or periodically. The countdown information is stored in the application.

The application provides functionality allowing the user to override the countdown information received from the storage device 100. At step 52 the application receives a countdown reset command via one or more user inputs of the user device 400. At step 54 the number of days remaining until a next injection is due is resent to the predefined initial value in the application.

The predefined value may be 14 days, but may itself be changed via the application. The application also creates a reset time stamp indicating the precise date and time of the reset. This information is stored in a reset history which may be viewed in chart from via the application.

At step 56, the application sends the countdown reset command, or information derived from the command, to the storage device 100. The application may be configured to send this information automatically in response to receiving the countdown reset command.

At step 58, the storage device 100 receives the countdown reset command and updates the number of days remaining until a next injection is due in its memory to the predefined initial value.

INDUSTRIAL APPLICATION

Figure 9:
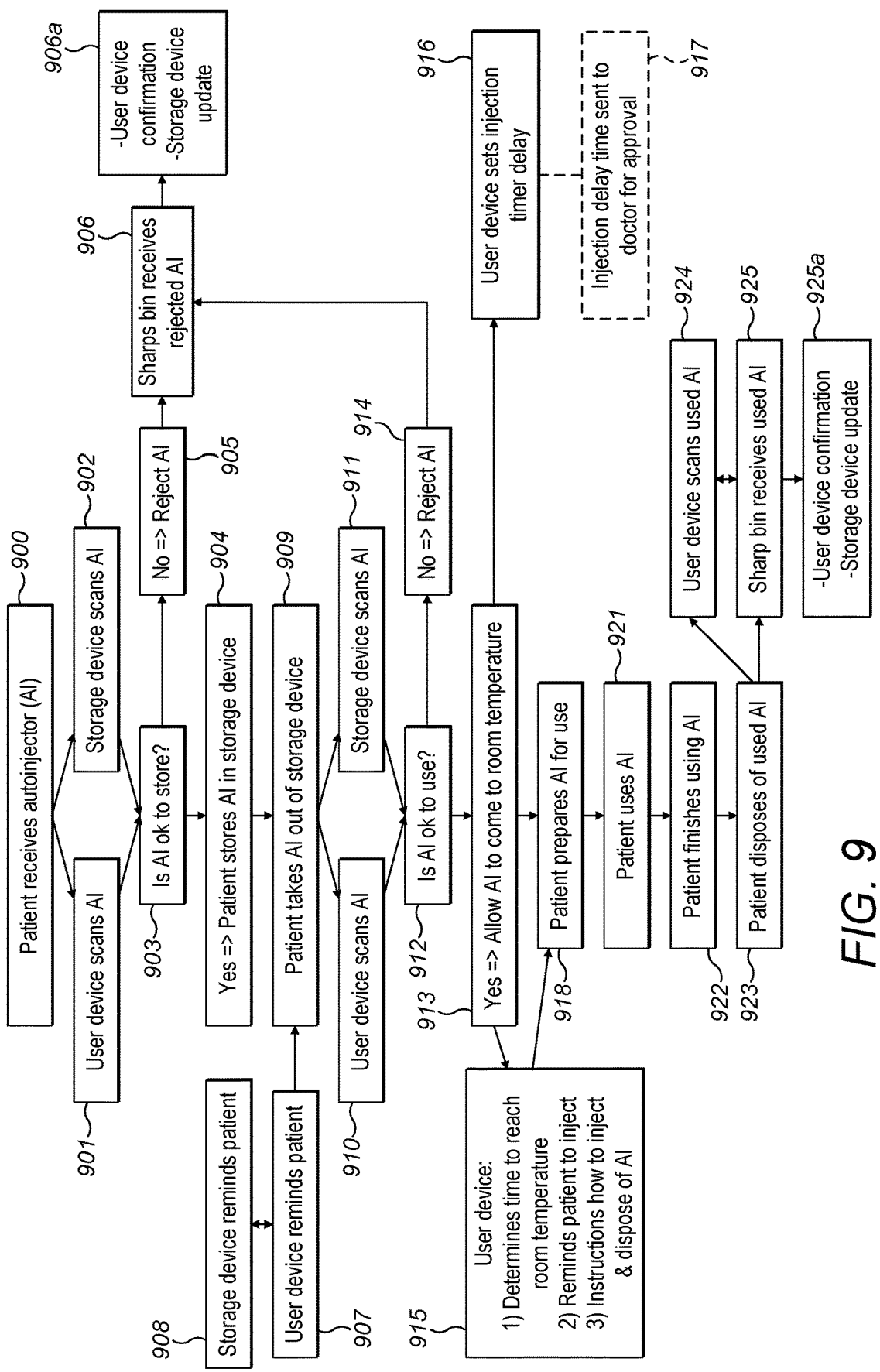
FIG. 9 is a flowchart illustrating exemplary use of an autoinjector by a user.

FIG. 9 is a flowchart illustrating exemplary use of an autoinjector by a user. As well as the functions and features explained above, various aspects of system 600 may allow the following use of injection device 10 by a patient. While the example shown if FIG. 9 refers to an autoinjector (AI), it is understood that one types of injection device 10 may be used. An autoinjector can also be referred to as a "pre-filled pen."

Initially, at step 900, a patient may receive injection device 10. Injection device 10 can include an autoinjector (AI). Injection device 10 (e.g., autoinjector) could be received via mail order, delivery service, or pick-up from a pharmacy. A package received by a patient can include one or more autoinjectors/injection devices 10. For example, a package could include six injection devices 10 representing 3 or 6 months supply. A single package of injection devices 10 could also include one or more autoinjectors containing different dosages of medicament.

Once received, a patient may scan one or more autoinjectors/injection devices 10 using user device 400 at step 901. It is also contemplated that storage device 100 could have similar functionality (step 902). For example, a patient may scan an autoinjector label before loading the autoinjector within storage device 100. As described above, injection device 10 can include a QR code, NFC or similar label containing various medicament, device, or other information. Where the injection device has a visible code, barcode, QR code or the like, this may be captured by the camera 410 of the user device 400. Alternatively, or in addition to the visible code, the injection device may comprise am RFID tag, which may be read by the RFID reader 418 of the user device 400.

Scanning by either user device 400 (step 901) or storage device 100 (step 902) could provide confirmation that the correct injection device 10 was received and correctly located for long-term in-home storage. User device 400 or storage device 100 may provide a confirmation that is sent to a third-party to confirm correct receipt and storage. Such signalling from two separate sources can provide additional assurances that the patient is compliant with appropriate receipt and storage instructions.

At step 903, the user device 400 and/or storage device 100 can determine whether the autoinjector is "OK," or appropriate, for storage. If the autoinjector is OK to store, at step 904, user device 400 or storage device 100 may then communicate this information to a database to confirm that the autoinjector is ok to store. This can include, for example, confirming that a patient has received an autoinjector containing a medicament that has been appropriately prescribed to this specific patient, the autoinjector contains the correct dosage of medicament, the medicament is unexpired (or will not expire by the time the patient uses the autoinjector), the medicament or autoinjector has not been recalled, the patient has not been prescribed another medicament that may adversely react to the medicament containing within the autoinjector, the patient's doctor has not modified the patient's therapy, or other reasons. If it is determined in step 903 that an autoinjector is ok to store, the patient may be instructed to place that autoinjector in storage device 100. If it is determined in step 903 that the autoinjector is not ok to store, then the patient may be instructed to dispose of the autoinjector in sharps bin 3 in step 905. In step 906 the sharps bin detects receipt of the rejected autoinjector.

User device 400 and/or sharps bin 3 may individually or cumulatively communicate one or more signals to confirm and/or reconfirm that the autoinjector has been appropriately disposed of in step 906a. In this step, upon receiving confirmation from the sharps bin 3 that the autoinjector has been appropriately disposed of, the user device 400 can update the information it stores to reflect that the rejected autoinjector was appropriately disposed of. Additionally, the user device 400 may send a confirmatory message to the sharps bin 3, storage device 100, or both. The information in the storage device 100 may then be updated to reflect that the rejected autoinjector was appropriately disposed of.

Following, system 600 may order the patient a replacement autoinjector. User device 400 may then provide a confirmation to the specific patient. A doctor or HCP may also provide additional information to the specific patient based on specific details associated with injection device 10.

After placing an autoinjector into storage device 100 (step 904), a patient may need to place another autoinjector into storage device 100. For example, if multiple injection devices 10 within a package all require storage, the user may either scan another injection device 10 using user device 400 (step 901) or storage device 100 (step 902).

After placing one or more autoinjectors into storage device 100 (step 904), a patient may wait for an extended period of time before needing to inject themselves. Typically, dosing for chronic diseases can occur every week, every two weeks, or once a month. Some may be less or more frequent, and some dosing schedules may vary. For example, initially a patient must dose every two weeks. Then after a time, the same patient could dose every four weeks.

It is also contemplated that a patient on a chronic therapy may not need to dose with a highly regular schedule. Certain chronic diseases may allow a patient to move a dosing forward or backwards by one or more days, without adverse consequences. For example, a patient may wish to dose themselves over a weekend rather than during the following week. Moving a dosing forward one or more days may not have a significant effect on the patient's therapy. Such a change to dosing schedule could require pre-approval by the patient's doctor.

User device 400 may provide a reminder to a patient to use an autoinjector/injection device 10 in step 907. For example, a notification may appear automatically on the display 412 of the user device 100 when the reminder time occurs. Alternatively, or in addition, storage device 100 may provide a reminder to a patient to use an autoinjector/injection device 10 in step 908. This reminder may be in the form of an audible alert emitted by the storage device. This may be accompanied by a visual alert, such as some or all of the segments of display 211 or a flashing of some or all of the LED array 220. In some embodiments, the reminders (or instructions to display a reminder) to use an autoinjector/injection device 10 are generated by the storage device 100 and then sent to the user device 400. As described above, the reminder may include audible or visual indicators from one or both devices. Providing multiple reminders from multiple sources may assist with adherence, particularly with chronic diseases that require dosing after extended intervals.

Other information may be transmitted between user device 400 and storage device 100 while injection device 10 is stored within storage device 100. One or both devices 400, 100 may update information associated with injection device 10. For example, storage device 100 may be configured to monitor local temperature. If the local temperature goes out of range for an extended period of time, storage device 100 may provide an alert to user device 400. User device 400 may determine that injection device 10 is still suitable for use if the cold chain of injection device 10 is broken for a short period of time. However, if the cold chain is broken for an extended period of time, user device 400 may signal to the user to dispose of injection device 10 as described above. These and other signals associated with the events of step 903 could also occur while injection device 10 is stored within storage device 100.

After such a reminder provided by step 907 and/or 908, the patient takes the autoinjector out of storage device 100 in step 909. The patient may then use user device 400 to scan the autoinjector as described above in step 910. Alternatively, storage device 100 may scan the autoinjector as it is removed from the refrigerator in step 911. At step 912, the user device 400 and/or storage device 100 can determine whether the autoinjector is OK to use. These can include events described above for step 903. If the autoinjector is OK to use, at step 913, both or either device 100, 400 may provide a signal to a remote server or database to confirm that the removed autoinjector is suitable for use. For the same reasons described above, it may not be appropriate for a patient to use a specific autoinjector. If not appropriate (step 914), the patient may then dispose of the rejected autoinjector in sharps bin 3 at step 906 and 906a, as described above. In general, signals exchanged between the user device and the storage device about a specific injection device may be referred to as a first set of signals and signals exchanged between the user device and the digital sharps bin about a specific injection device may be referred to as a second set of signals.

If determined that a specific autoinjector/injection device 10 is appropriate to use, user device 400 may determine how long that autoinjector should remain outside the refrigerator until its temperature rises to an acceptable level at step 915. User device 400 may calculate the time based at least in part on the type of autoinjector/injection device 10, the type and volume of medicament within the autoinjector, the temperature of the room, the forecast temperature for the location of the autoinjector, or other factors. As part of step 915, the time may be provided to the patient through a timing interface. The timing interface may provide an audible signal when the time expires. User device 400 may also provide instructions to the patient on how to use and/or dispose of the autoinjector. This could include, if needed, how to remove the cap, how to perform a priming shot, how to attach a needle, how to inject, how to confirm a complete dose was injected, and how to safely dispose of the autoinjector.

In some situations, it may also be possible for a patient to decide after the autoinjector has been removed from the refrigerator that they do not wish to administer the dose that day. For various reasons, the patient may decide to wait a day or more. Instead of putting the autoinjector back into storage device 100, the patient may leave the autoinjector at room temperature. Such dosing may be permitted via prior approval of the patient's doctor, and the doctor may be notified before or after the fact.

If a patient decides that they want to delay their injection, user device 400 may allow the patient to set another timer at step 916. This second timer may have a limit of one or more days, limiting the number of days that a patient could delay their dosing. Desired time delay, doctor approval, autoinjector location, and other information may be input or received via user device 400. Optionally, at step 917, the desired injection delay time may be communicated to a Doctor for approval.

At step 918, the patient prepares the autoinjector for use. Once a patient decides to dose themselves, they may use user device 400 to take one or more actions (not shown). They could, for example, use user device 400 to scan the autoinjector to indicate one or more events. This could include an approximate start of injection time point.

As described above, the patient may use the autoinjector/injection device 10 to self-inject a dose of medicament at step 921. For an autoinjector, this may include removing a cap from the autoinjector, placing the correct end of the autoinjector against the patient's skin at a specific location (e.g., often the stomach or upper leg), administering the dose of medicament, then removing the autoinjector once the injection process is complete.

Once the injection is complete (step 922), the patient may or may not recap the autoinjector. The patient may also perform another step using user device 400. For example, scan the autoinjector.

Following injection at step 922, a patient or person assisting the patient with the process may enter various information into user device 400. For example, an image of the injection site may be taken, an indication of the injection process may be recorded, a pain rating, etc. Such information may be associated with a time stamp for later analysis.

The patient may then dispose of the autoinjector/injection device 10 at step 923. Such disposal can include placing the used autoinjector into sharps bin 3, which can detect receipt of the used autoinjector in step 925. In step 925a, upon receiving confirmation from the sharps bin 3 that the autoinjector has been appropriately disposed of, the user device 400 can be updated with the information it stores to reflect that the used autoinjector was appropriately disposed of. Additionally, the user device 400 may send a confirmatory signal to one or more sources within system 600. Alternatively, at step 924, the user may scan the used AI with user device 400. This information may then be provided to other sources within system 600 by user device 400 without the use of sharps bin 3.

Various parts of system 600 may be notified once an injection device 10 is successfully disposed of. As described above, having multiple data provided by multiple devices can improve adherence and improve safe disposal of autoinjectors/injection devices 10. In addition, as provided at steps 906a and 925a, user device 400 may provide a confirmation that injection device 10 has been successfully disposed of.

In some embodiments, storage device 100, user device 400, and/or sharps bin 3 may provide a signal to indicate that another autoinjector/injection device 10 should be delivered to a patient. Such signally or ordering can occur after every disposal of injection device 10, or can occur after a predefined number of devices have been disposed of. For example, if packages of 2, 4, or 6 injection devices 10 are available, system 600 may only re-order 2, 4, or 6 injection devices after that many devices have been disposed of. Various numbers of injection devices 10 are possible within one or more packages.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with an injection device 10. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the injection devices 10 as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in injection device 10. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A system comprising:
a user device comprising a processor, a memory, and a wireless transceiver; and
a storage device configured to communicate wirelessly with the user device, the storage device comprising:
a plurality of openings, wherein each opening is configured to store an unused injection device for a period of time and wherein each opening has an associated sensor, and
a storage device wireless transceiver, wherein the user device is configured to:
scan a first injection device to determine at least one of a drug dosage contained within the first injection device and a device expiration date of the first injection device, and
create first device data relating to at least one of the drug dosage and the device expiration date and associate the first device data with a first opening of the plurality of openings of the storage device, and
wherein the storage device is configured to:
detect whether the first injection device has been placed in, or removed from, the first opening.

2. The system of claim 1, wherein the storage device is configured to send a signal to the user device indicating which one of the plurality of openings an injection device was placed in or removed from.

3. The system of claim 2, wherein the user device is configured:
subsequent to receiving the signal from the storage device, to confirm whether the first injection device was placed in or removed from the first opening or a second opening;
if the first injection device was placed in or removed from the first opening, to output a confirmation message; and
if the first injection device was placed in or removed from a second opening, to output an alert.

4. The system of claim 1, wherein each associated sensor is configured to determine an identifier of an injection device stored in the associated opening and wherein the storage device is configured to send a signal to the user device indicating which one of the plurality of openings an injection device was placed in or removed from and the identifier of the injection device.

5. The system of claim 1, wherein the user device is configured to transmit to the storage device an indication of which of the plurality of openings is the first opening.

6. The system of claim 5, wherein each of the plurality of openings has at least one LED and after receiving the indication of which of the plurality of openings is the first opening from the user device, the storage device is configured to illuminate one or more of the at least one LED associated with the first opening.

7. The system of claim 1, wherein the user device is configured to:
display a representation of the storage device;
indicate which of the plurality of openings is the first opening on the representation; and
indicate that the first injection device should be placed into the first opening on the representation.

8. The system of claim 7, wherein upon determining that an injection is due, the user device is configured to indicate on the representation of the storage device which of the plurality of openings to remove an injection device from.

9. The system of claim 1, wherein upon determining that an injection is due, the user device is configured to transmit to the storage device an indication of which of the plurality of openings to remove an injection device from.

10. The system of claim 9, wherein each of the plurality of openings has at least one associated LED and after receiving from the user device the indication of which of the plurality of openings to remove an injection device from, the storage device is configured to illuminate one or more of the at least one LED associated with the indicated opening.

11. The system of claim 10, wherein in response to determining that the storage device contains several injection devices having the same drug dosage, the user device is configured to select the injection device having the earliest expiration date and to indicate the opening containing the injection device having the earliest expiration date on the representation of the storage device and/or by transmitting the indication to the storage device.

12. The system of claim 11, wherein in response to determining that two different injection devices need to be used, the user device is configured to indicate two openings of the storage device and to differentiate between the two openings on the representation of the storage device and/or by signalling to the storage device.

13. The system of claim 12, wherein the user device is configured to indicate an order in which the two different injection devices need to be used on the representation of the storage device and/or by signalling to the storage device.

14. The system of claim 1, wherein the user device is configured to:
scan a second injection device to determine at least one of a drug dosage contained within the second injection device and a device expiration date of the second injection device; and
create second device data relating to at least one of the drug dosage and the device expiration date and associate the second device data with a second opening of the plurality of openings of the storage device,
wherein the storage device is configured to:
detect whether the second injection device has been placed in, or removed from, the second opening.

15. A method of operating a storage device the method comprising:
scanning a first injection device to determine at least one of a drug dosage contained within the first injection device and a first injection device expiration date of the first injection device, the first injection device being stored in a storage device comprising a plurality of openings, wherein each opening being configured to store an unused injection device for a period of time and wherein each opening has an associated sensor, and a storage device wireless transceiver;
creating first device data relating to at least one of the drug dosage and the first injection device expiration date and associate the first device data with a first opening of the plurality of openings of the storage device; and
detecting whether the first injection device has been placed in, or removed from, the first opening.

16. The method of claim 15, further comprising:
sending a signal to a user device indicating which one of the plurality of openings an injection device was placed in or removed from.

17. The method of claim 16, further comprising:
receiving a confirmation that the first injection device was placed in or removed from the first opening or a second opening;
generating a confirmation message; and
transmit an alert based on the confirmation message.

18. The method of claim 15, further comprising:
determining an identifier of the first injection device.

19. The method of claim 15, further comprising:
transmitting to the storage device an indication of which of the plurality of openings is the first opening.

20. The method of claim 15, further comprising:
displaying a representation of the storage device;
indicating which of the plurality of openings is the first opening on the representation; and
indicating that the first injection device should be placed into the first opening on the representation.

* * * * *